(12) United States Patent
Hirayama et al.

(10) Patent No.: US 11,266,294 B2
(45) Date of Patent: Mar. 8, 2022

(54) IMAGE PROCESSING DEVICE, ENDOSCOPIC SURGERY SYSTEM, AND IMAGE PROCESSING METHOD

(71) Applicant: SONY CORPORATION, Tokyo (JP)

(72) Inventors: Tomoyuki Hirayama, Kanagawa (JP); Daisuke Kikuchi, Kanagawa (JP); Yuki Sugie, Kanagawa (JP); Yasuhiro Matsuda, Tokyo (JP); Daisuke Nagao, Kanagawa (JP); Takara Kasai, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 644 days.

(21) Appl. No.: 16/080,120

(22) PCT Filed: Feb. 21, 2017

(86) PCT No.: PCT/JP2017/006341
§ 371 (c)(1),
(2) Date: Aug. 27, 2018

(87) PCT Pub. No.: WO2017/154577
PCT Pub. Date: Sep. 14, 2017

(65) Prior Publication Data
US 2019/0059696 A1    Feb. 28, 2019

(30) Foreign Application Priority Data
Mar. 9, 2016    (JP) .............................. JP2016-045440

(51) Int. Cl.
*A61B 1/00*     (2006.01)
*A61B 90/50*    (2016.01)
(Continued)

(52) U.S. Cl.
CPC ...... *A61B 1/00006* (2013.01); *A61B 1/00009* (2013.01); *A61B 1/0016* (2013.01);
(Continued)

(58) Field of Classification Search
CPC ............ A61B 1/00006; A61B 1/00009; A61B 1/00045; A61B 1/00149; A61B 1/0016;
(Continued)

(56) References Cited

U.S. PATENT DOCUMENTS

| 5,032,913 A * | 7/1991 | Hattori ................. H04N 9/0455 348/70 |
| 2006/0164647 A1 * | 7/2006 | Shibata .................. G01N 21/89 356/430 |

(Continued)

FOREIGN PATENT DOCUMENTS

| CN | 103096781 A | 5/2013 |
| JP | 01-136625 A | 5/1989 |

(Continued)

OTHER PUBLICATIONS

Office Action for JP Patent Application No. 2016-045440, dated Dec. 10, 2019, 03 pages of Office Action and 03 pages of English Translation.

(Continued)

*Primary Examiner* — Timothy J Neal
*Assistant Examiner* — William B Chou
(74) *Attorney, Agent, or Firm* — Chip Law Group

(57) ABSTRACT

Provided is an image processing device including: an image processing unit that generates image data for output from a captured image of an inside of a body cavity of a patient photographed by an endoscope. The image processing unit generates the image data in a manner that, when a lens barrel of the endoscope is moved in an optical axis direction of an objective lens during photographing, a display range in the captured image that is a range expressed in a display image
(Continued)

displayed on a display device does not change, during the movement and after the movement, from a display range before the movement.

21 Claims, 16 Drawing Sheets

(51) Int. Cl.
    *A61B 1/313*     (2006.01)
    *A61B 90/00*     (2016.01)
    *G02B 23/24*     (2006.01)
    *G06T 7/593*     (2017.01)
    *A61B 18/14*     (2006.01)
    *A61B 17/32*     (2006.01)
    *A61B 34/30*     (2016.01)
    *A61B 34/20*     (2016.01)
    *G03B 13/36*     (2021.01)
    *A61B 1/12*     (2006.01)
    *A61B 18/00*     (2006.01)

(52) U.S. Cl.
    CPC ...... *A61B 1/00045* (2013.01); *A61B 1/00149* (2013.01); *A61B 1/00188* (2013.01); *A61B 17/320068* (2013.01); *A61B 18/14* (2013.01); *A61B 18/1442* (2013.01); *A61B 34/30* (2016.02); *A61B 90/361* (2016.02); *A61B 90/50* (2016.02); *G02B 23/2476* (2013.01); *G06T 7/593* (2017.01); *A61B 1/127* (2013.01); *A61B 1/3132* (2013.01); *A61B 34/20* (2016.02); *A61B 90/37* (2016.02); *A61B 2018/00345* (2013.01); *A61B 2090/061* (2016.02); *G02B 23/2484* (2013.01); *G03B 13/36* (2013.01); *G06T 2207/10068* (2013.01); *G06T 2207/30004* (2013.01)

(58) Field of Classification Search
    CPC ... A61B 1/00188; A61B 1/127; A61B 1/3132; A61B 90/50; A61B 90/361; A61B 90/37; G02B 23/2484; G02B 23/2476
    See application file for complete search history.

(56) References Cited

U.S. PATENT DOCUMENTS

| | | | |
|---|---|---|---|
| 2006/0225994 A1* | 10/2006 | Onishi | C23C 18/166 200/181 |
| 2009/0076368 A1* | 3/2009 | Balas | A61B 1/00149 600/407 |
| 2009/0245600 A1 | 10/2009 | Hoffman et al. | |
| 2011/0184272 A1* | 7/2011 | Zeng | A61B 1/043 600/407 |
| 2013/0165753 A1 | 6/2013 | Takahashi | |
| 2013/0189641 A1* | 7/2013 | Perfect | A61B 1/24 433/29 |
| 2014/0005475 A1 | 1/2014 | Song et al. | |
| 2014/0005484 A1 | 1/2014 | Charles | |
| 2016/0324398 A1* | 11/2016 | Sasaki | G06T 7/0012 |

FOREIGN PATENT DOCUMENTS

| | | |
|---|---|---|
| JP | 05-049599 A | 3/1993 |
| JP | 05-292491 A | 11/1993 |
| JP | 05-337118 A | 12/1993 |
| JP | 08-164148 A | 6/1996 |
| JP | 2007-301226 A | 11/2007 |
| JP | 2012-055498 A | 3/2012 |
| JP | 2015-136470 A | 7/2015 |
| TW | 201400075 A | 1/2014 |
| WO | 2012/032914 A1 | 3/2012 |

OTHER PUBLICATIONS

Office Action for CN Patent Application No. 201780014765.2, dated Jul. 20, 2020, 5 pages of Office Action and 08 pages of English Translation.
International Search Report and Written Opinion of PCT Application No. PCT/JP2017/006341, dated Oct. 5, 2017, 15 pages of ISRWO.
Office Action for EP Patent Application No. 17710063.3, dated Feb. 17, 2021, 4 pages of Office Action.
Office Action for JP Patent Application No. 2020-139375, dated Aug. 3, 2021, 03 pages of Office Action and 05 pages of English Translation.

* cited by examiner

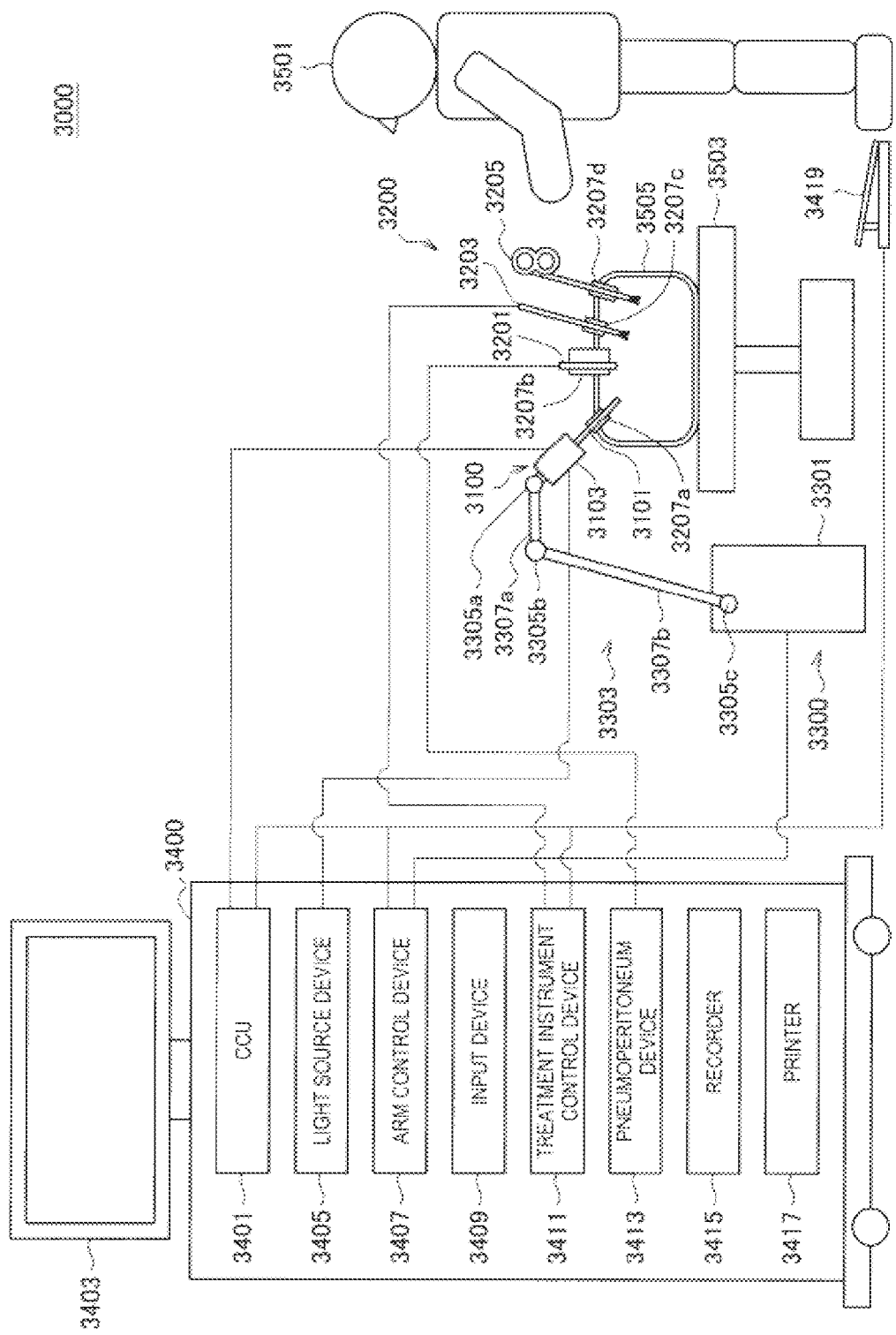
[Fig. 1]

[Fig. 2]
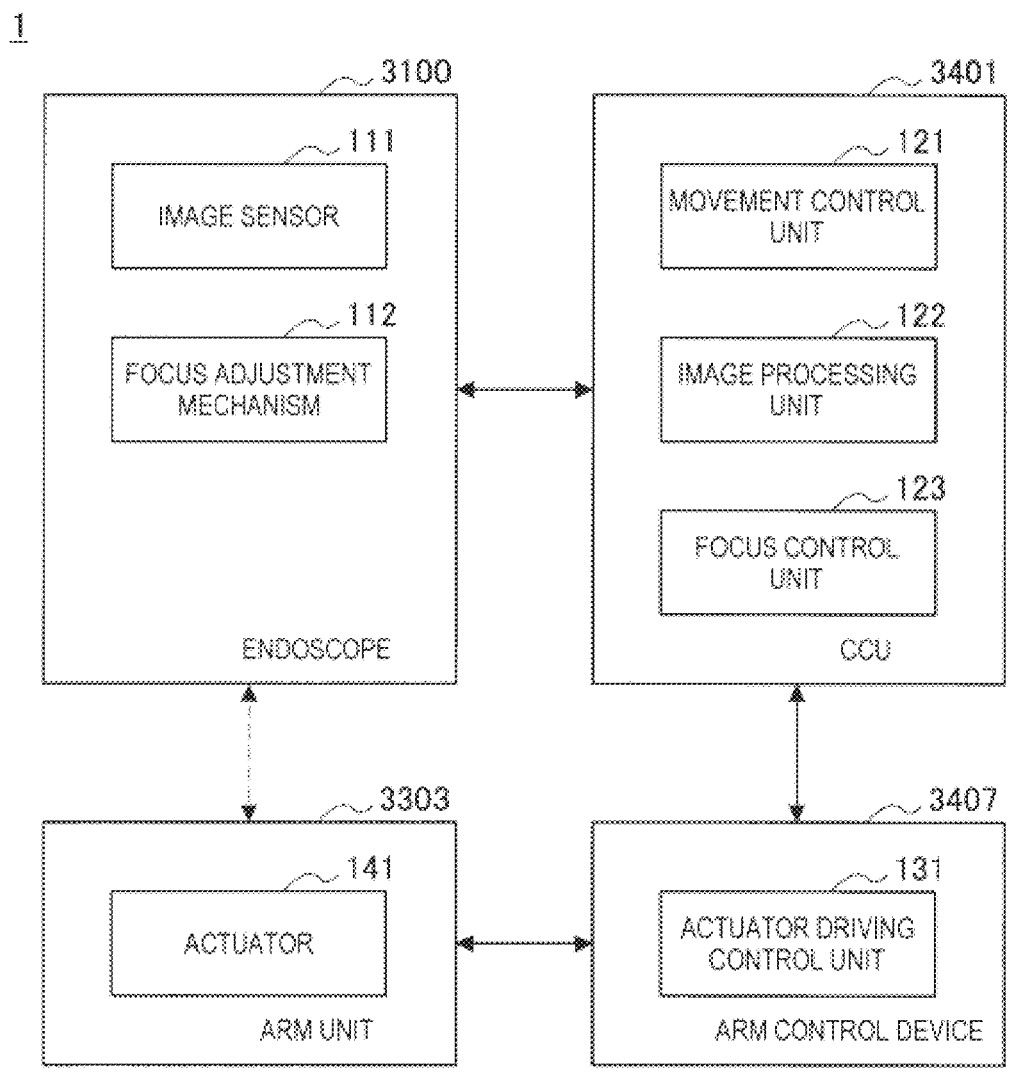

[Fig. 3A]
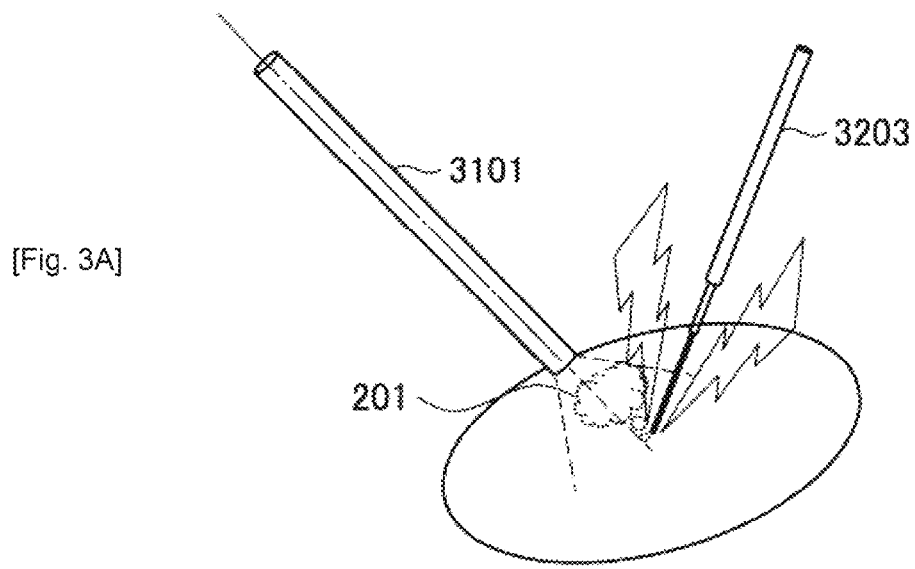
[Fig. 3B]
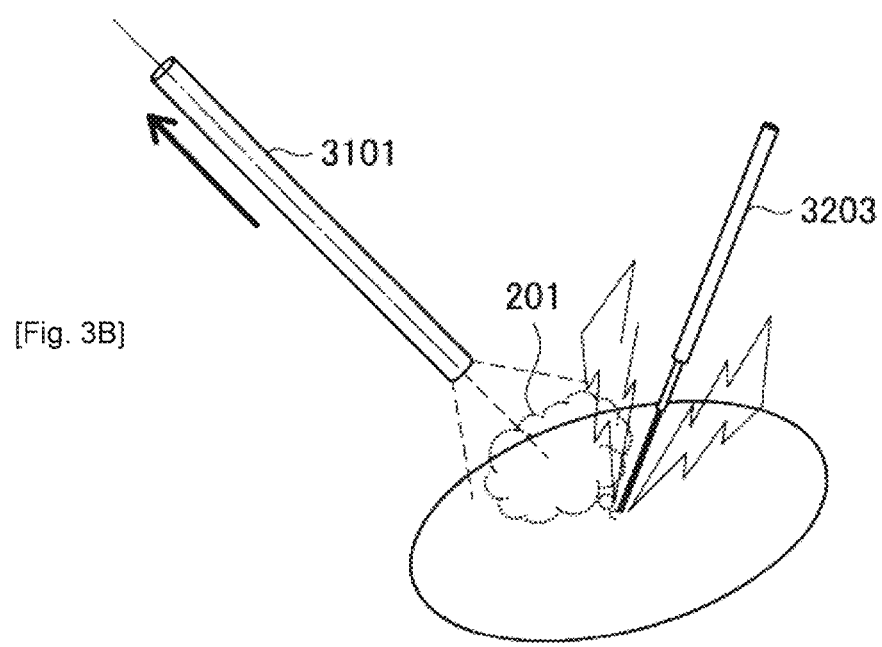

[Fig. 4]
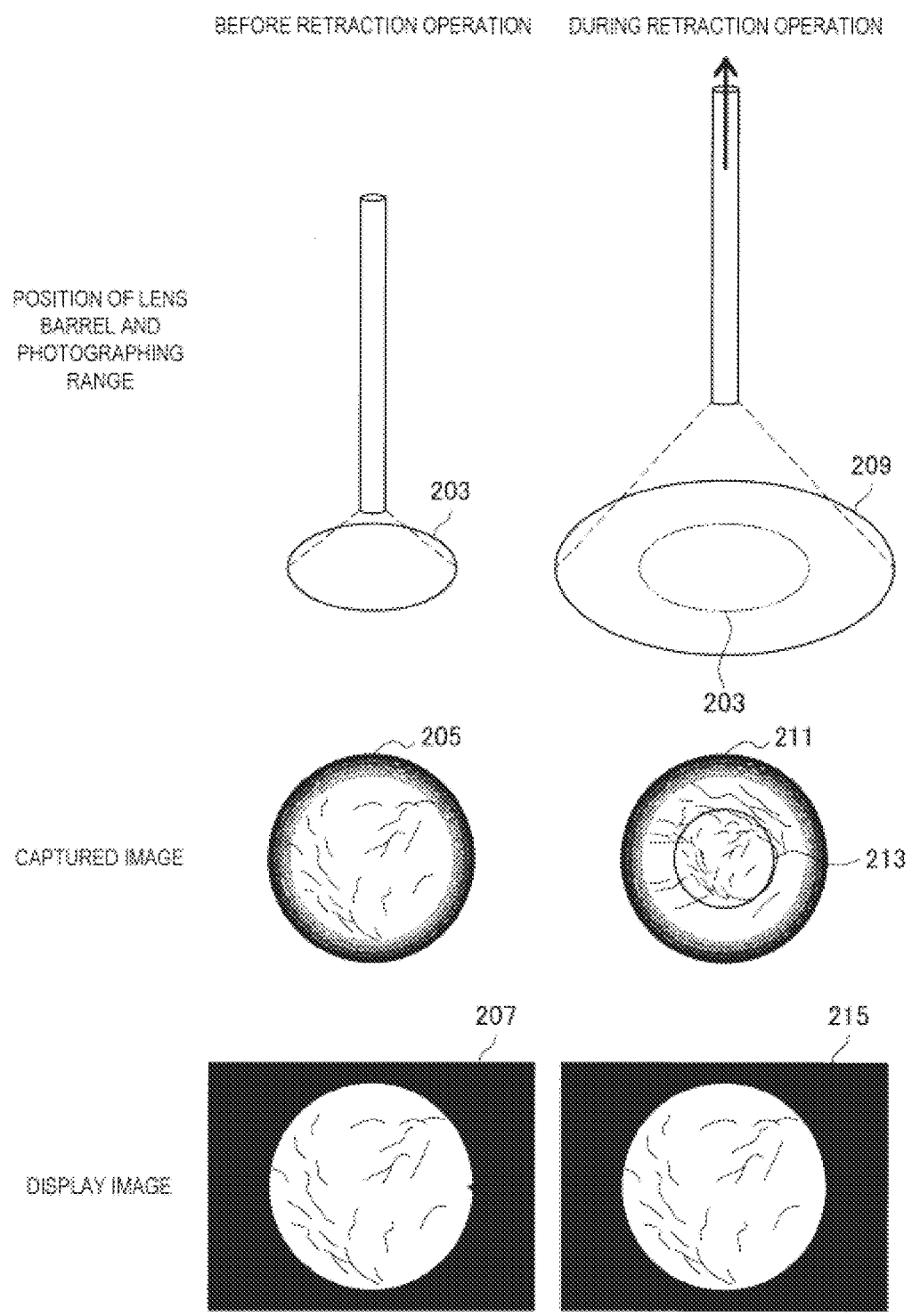

[Fig. 5]
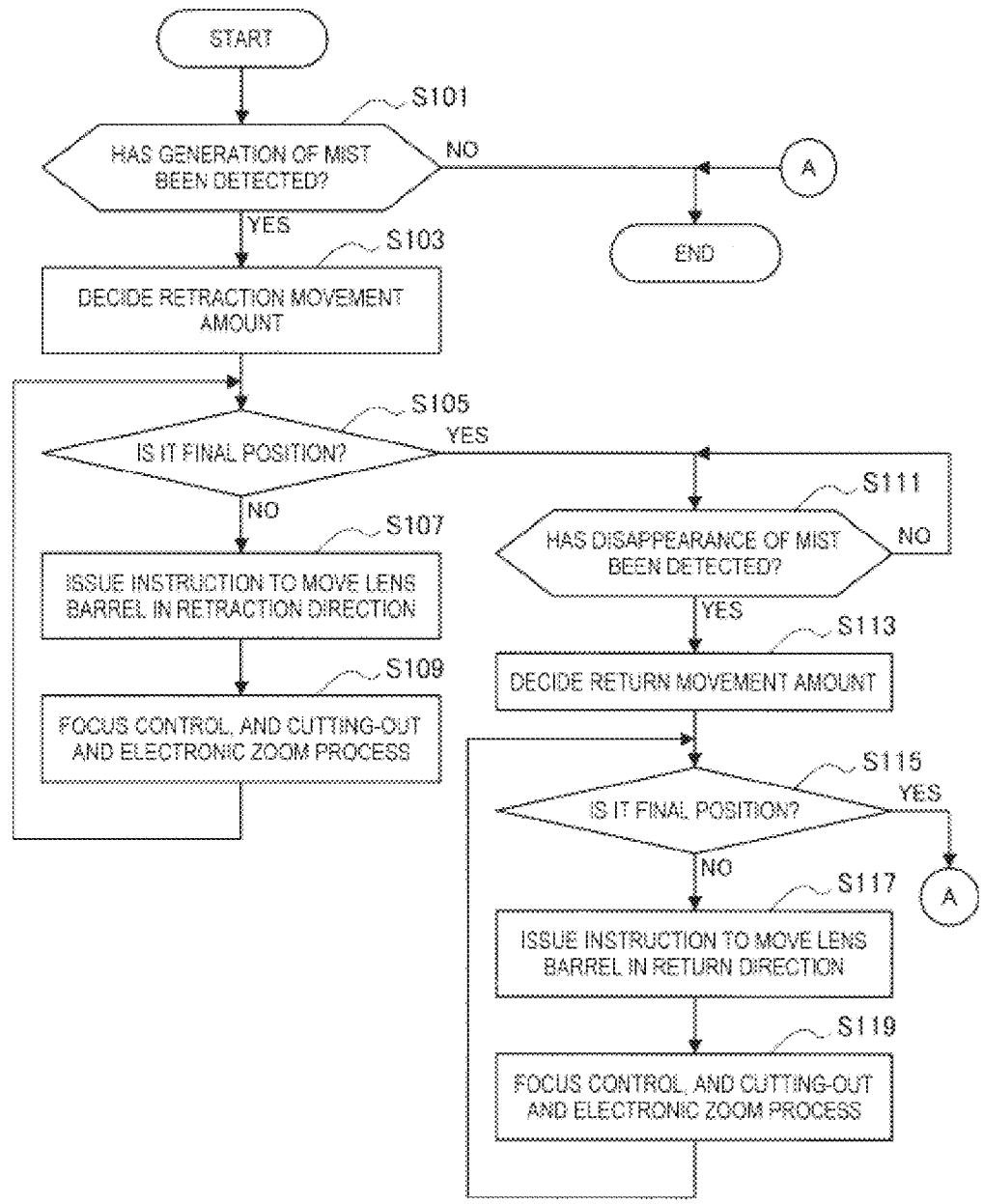

[Fig. 6]
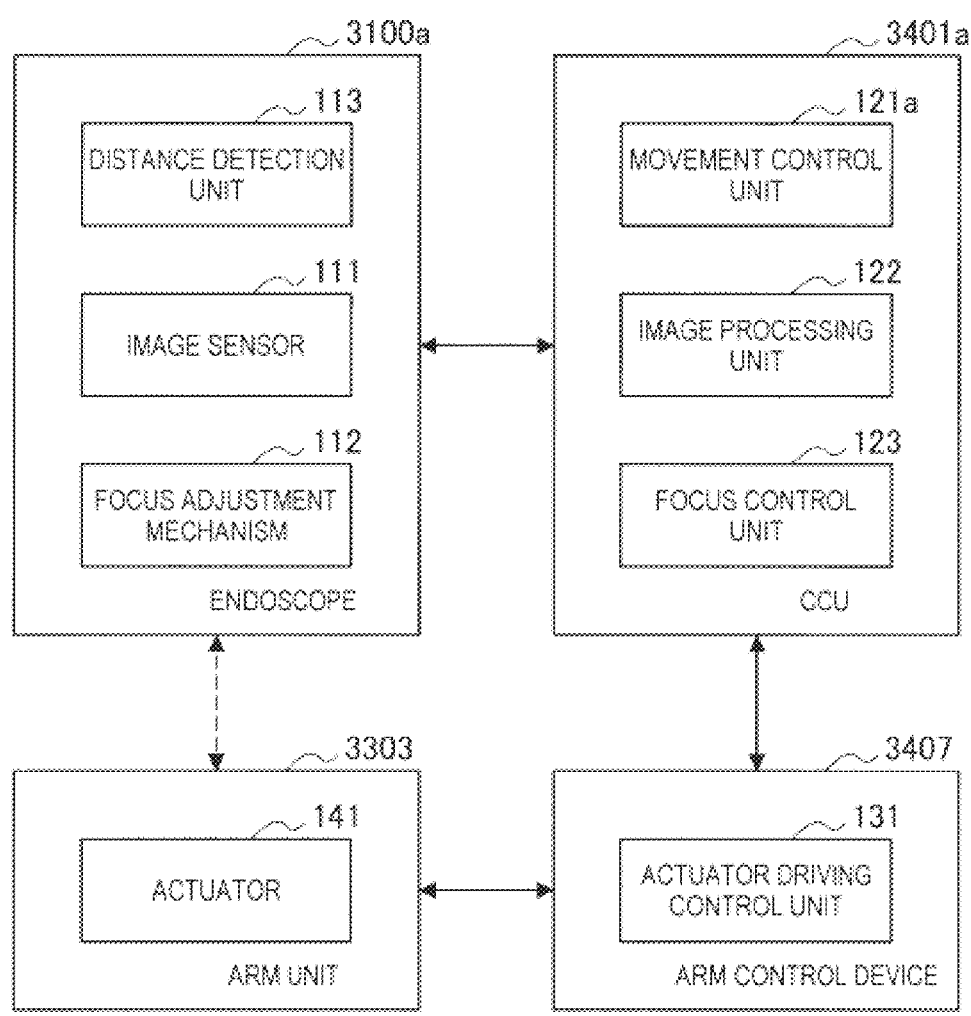

[Fig. 7]
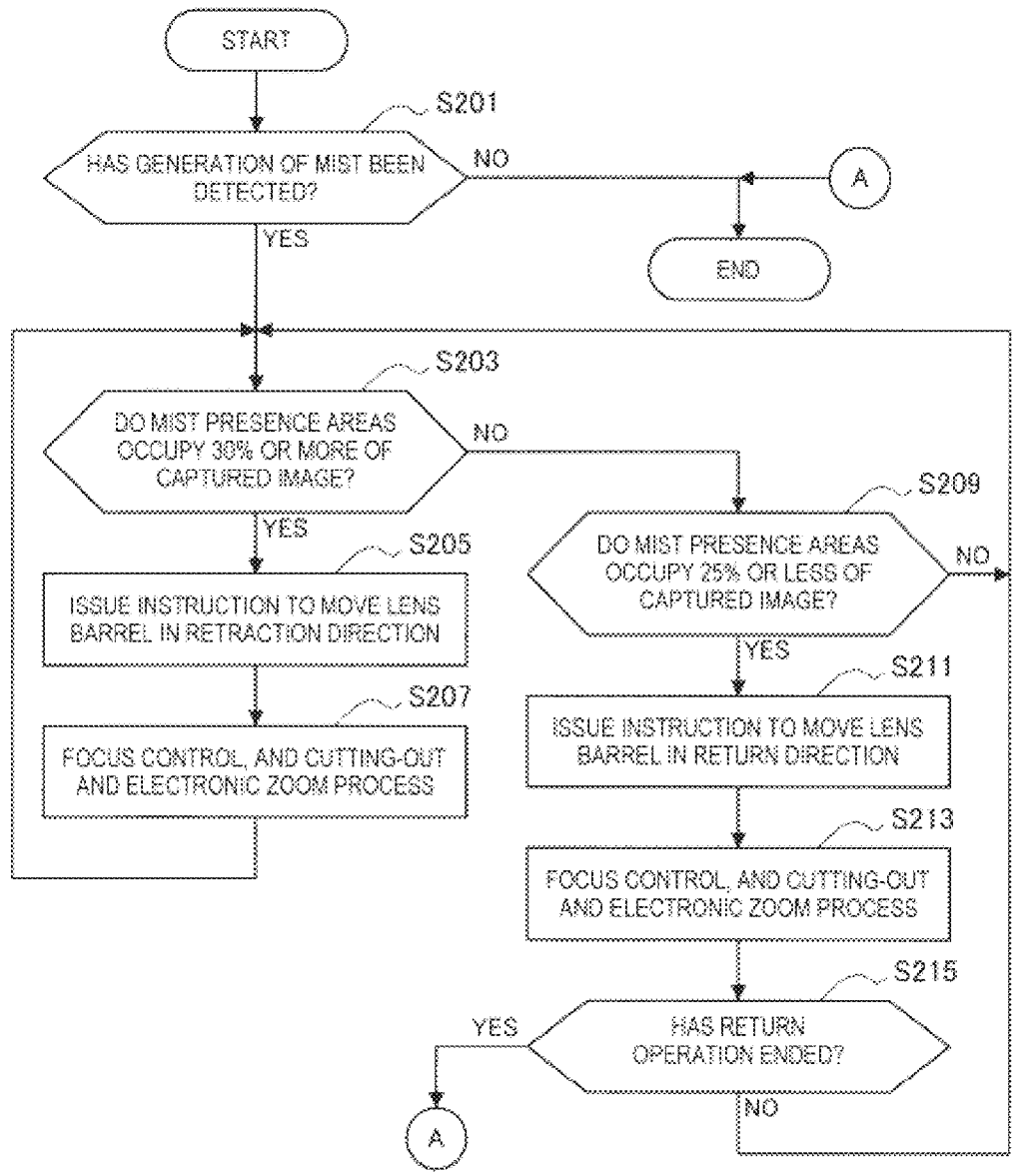

[Fig. 8A]
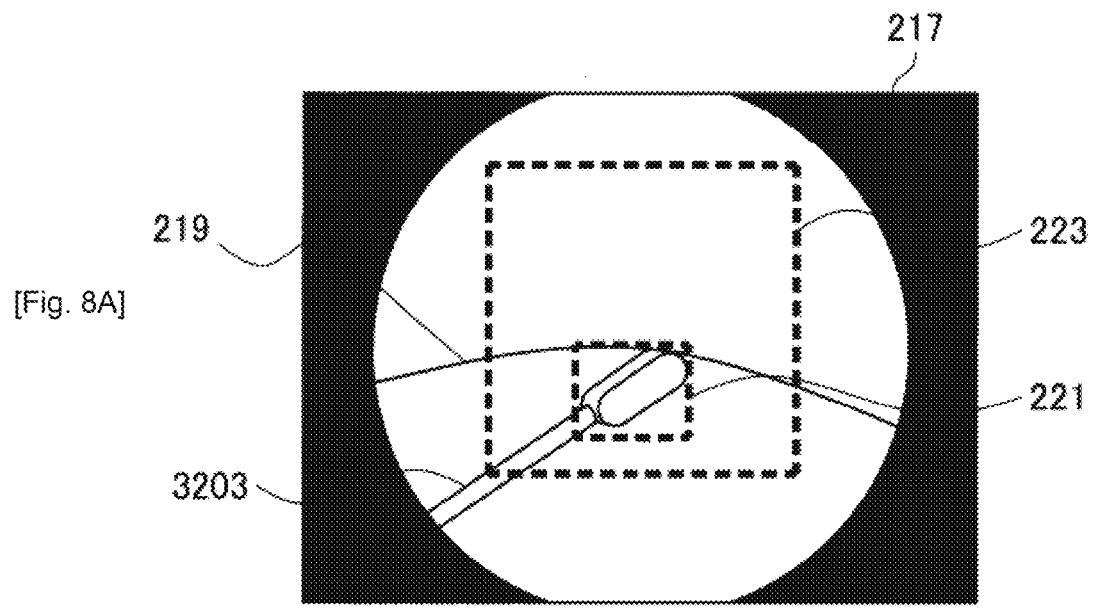
[Fig. 8B]
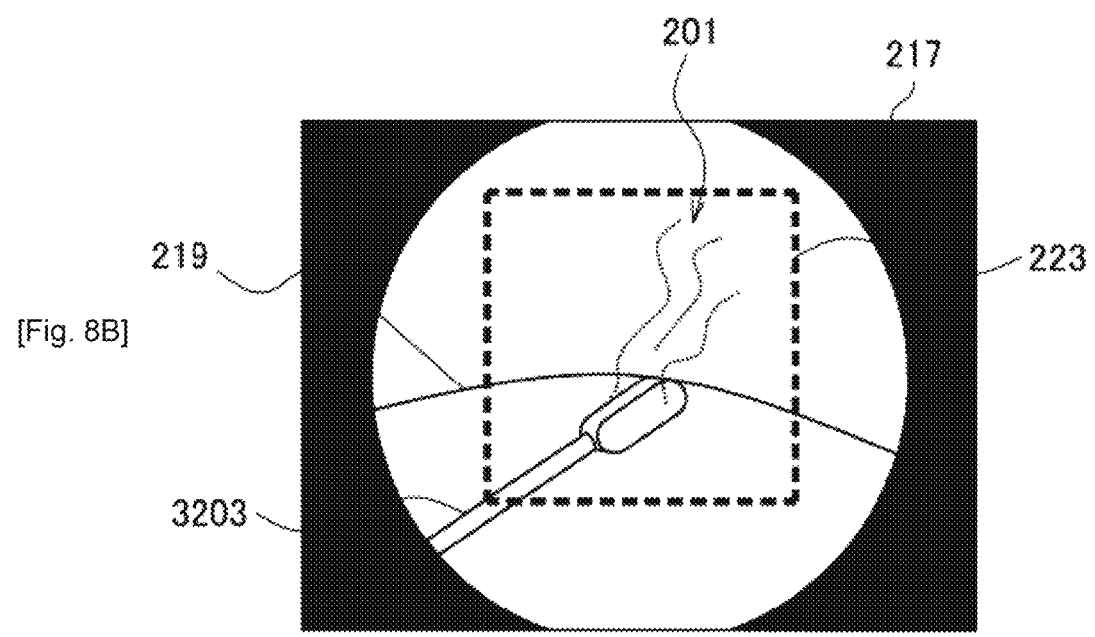

[Fig. 9A]
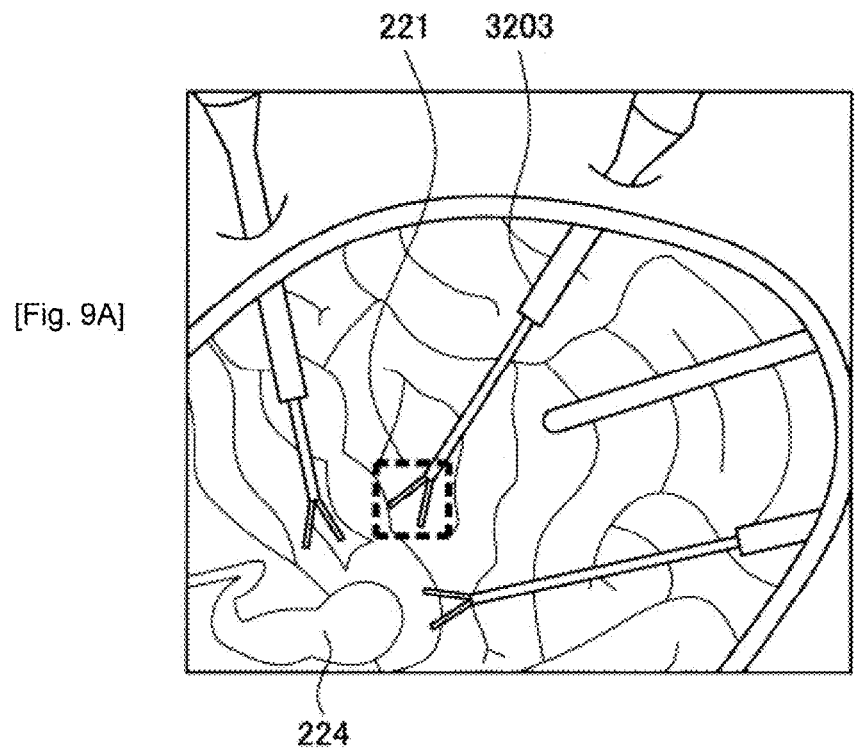
[Fig. 9B]
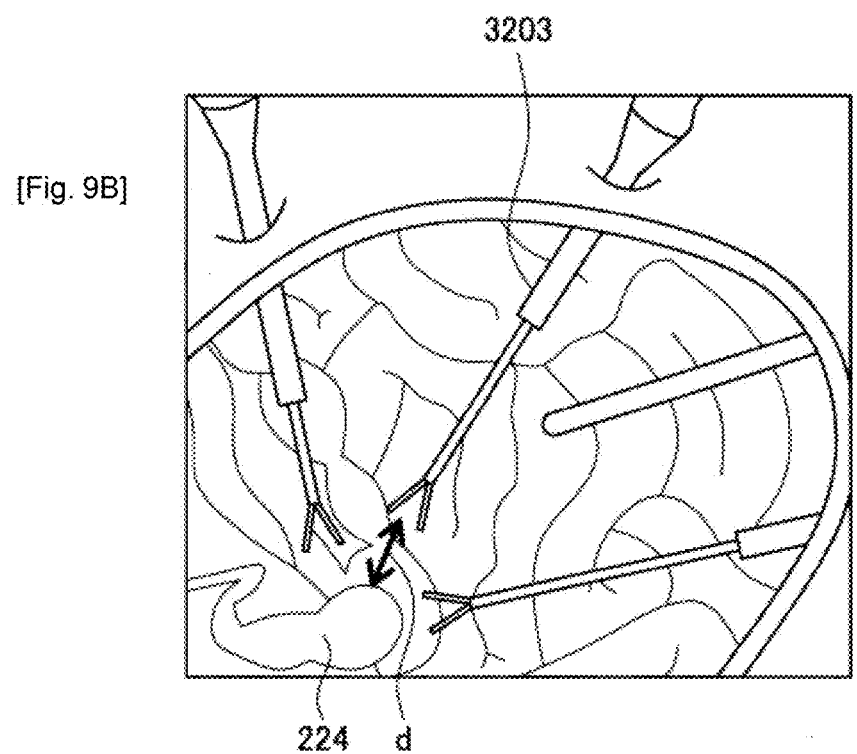

[Fig. 10]
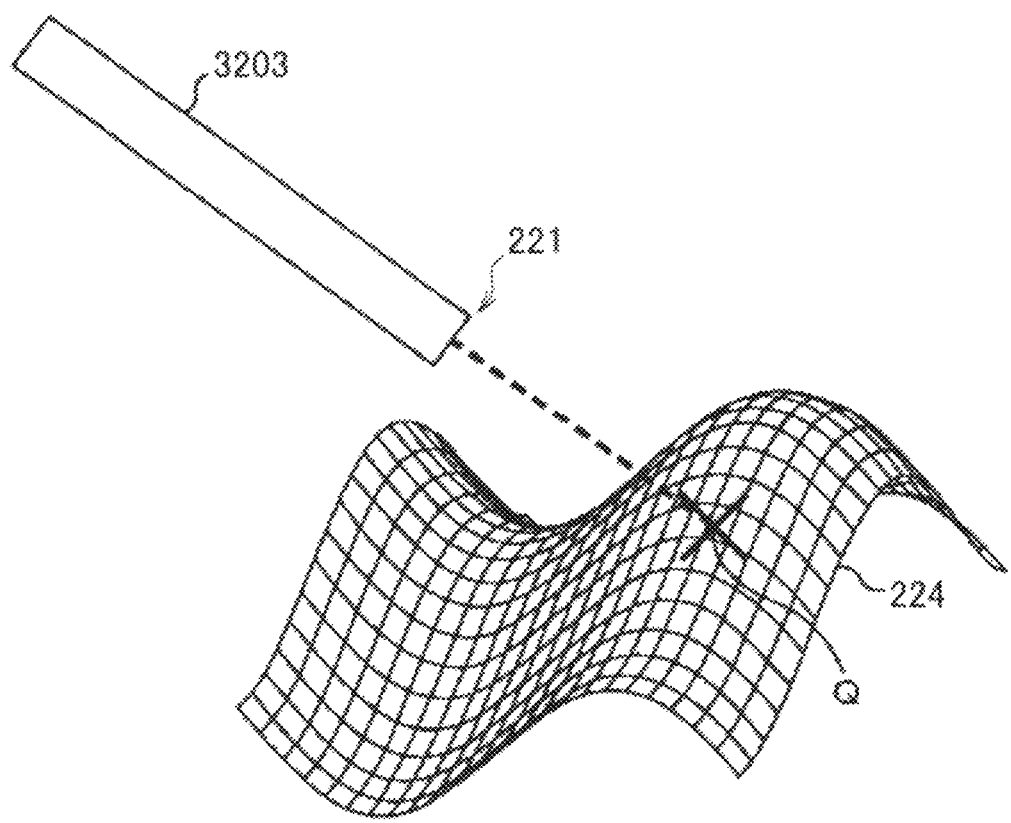

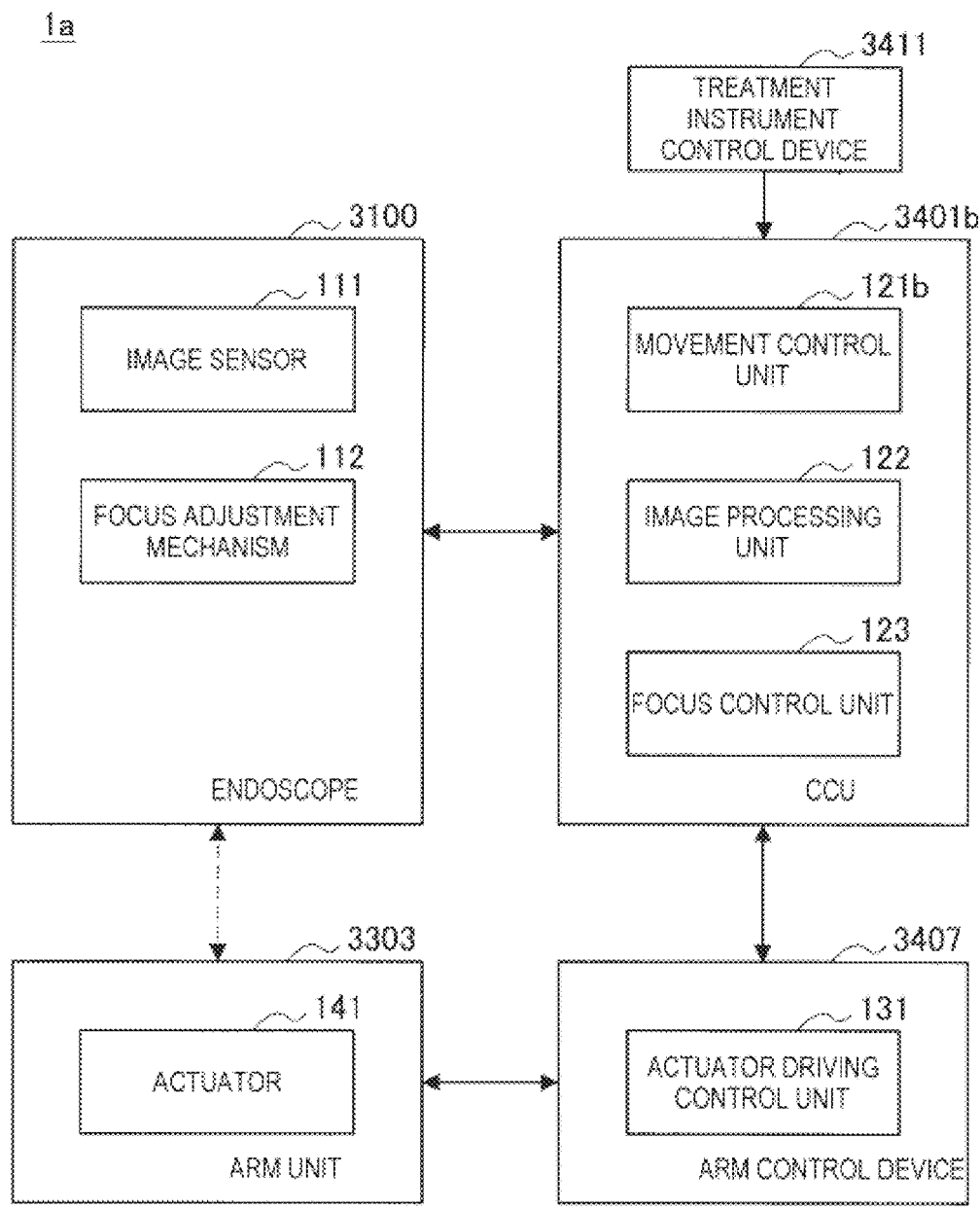
[Fig. 11]

[Fig. 12]
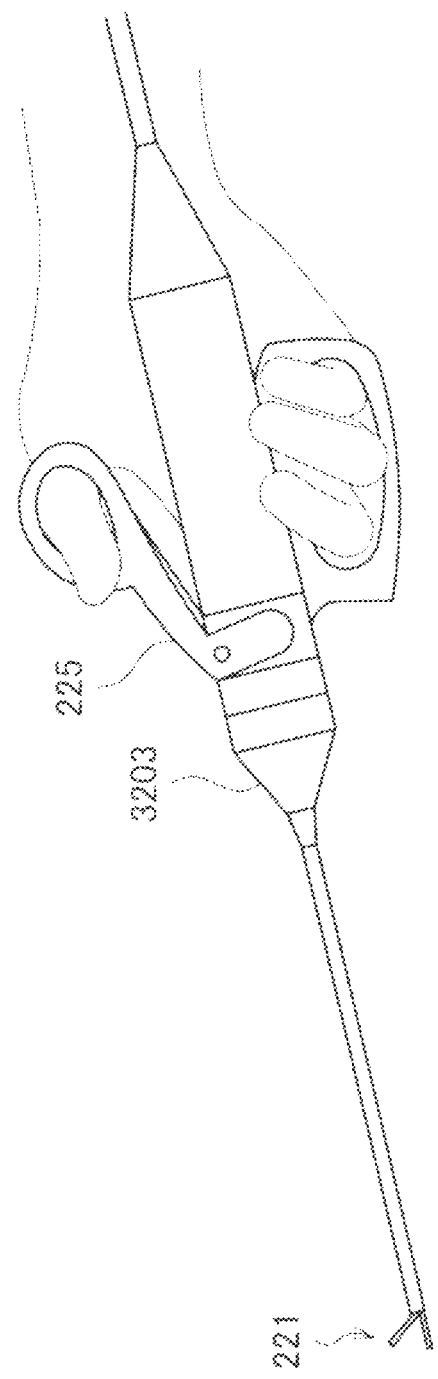

[Fig. 13]
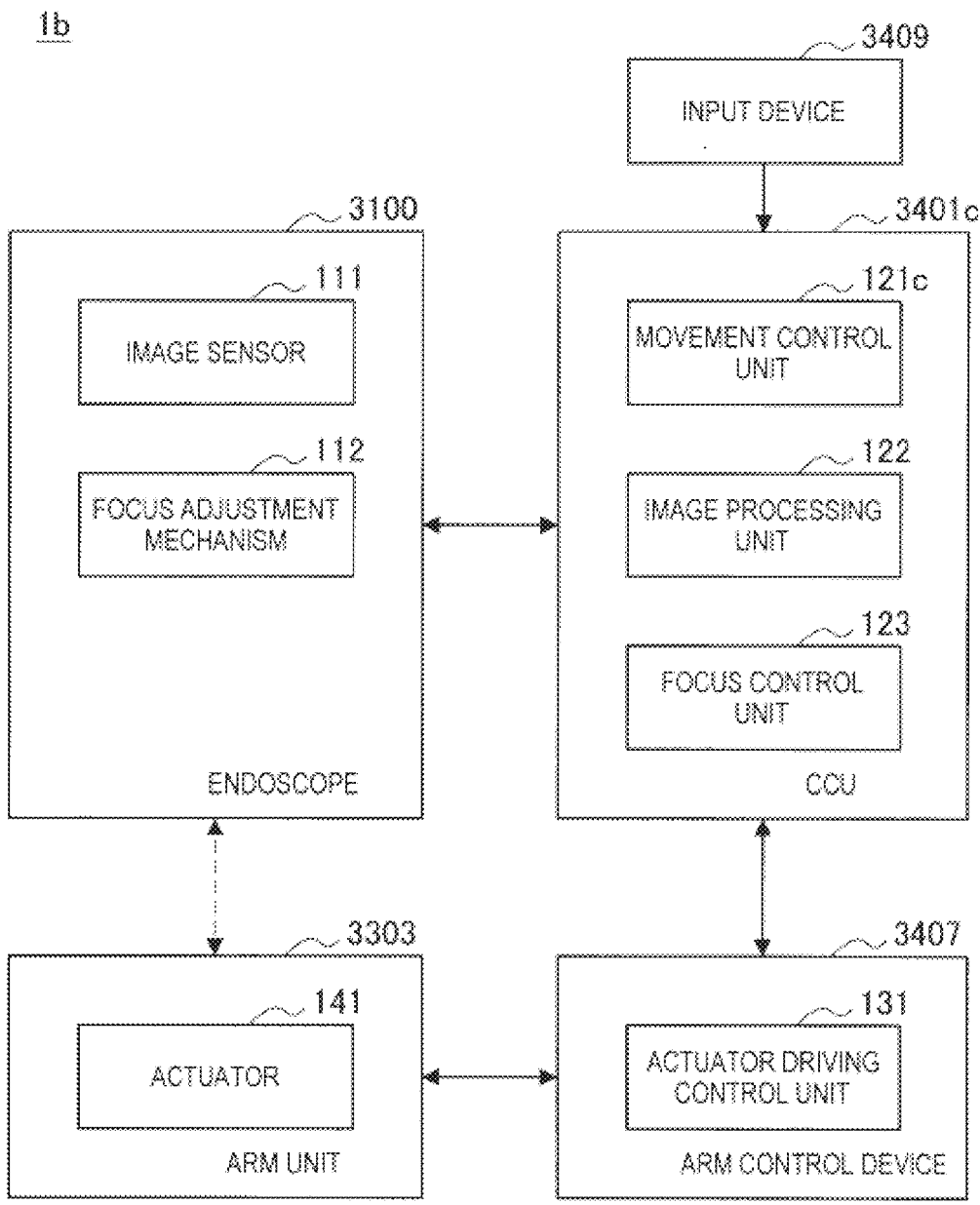

[Fig. 14]
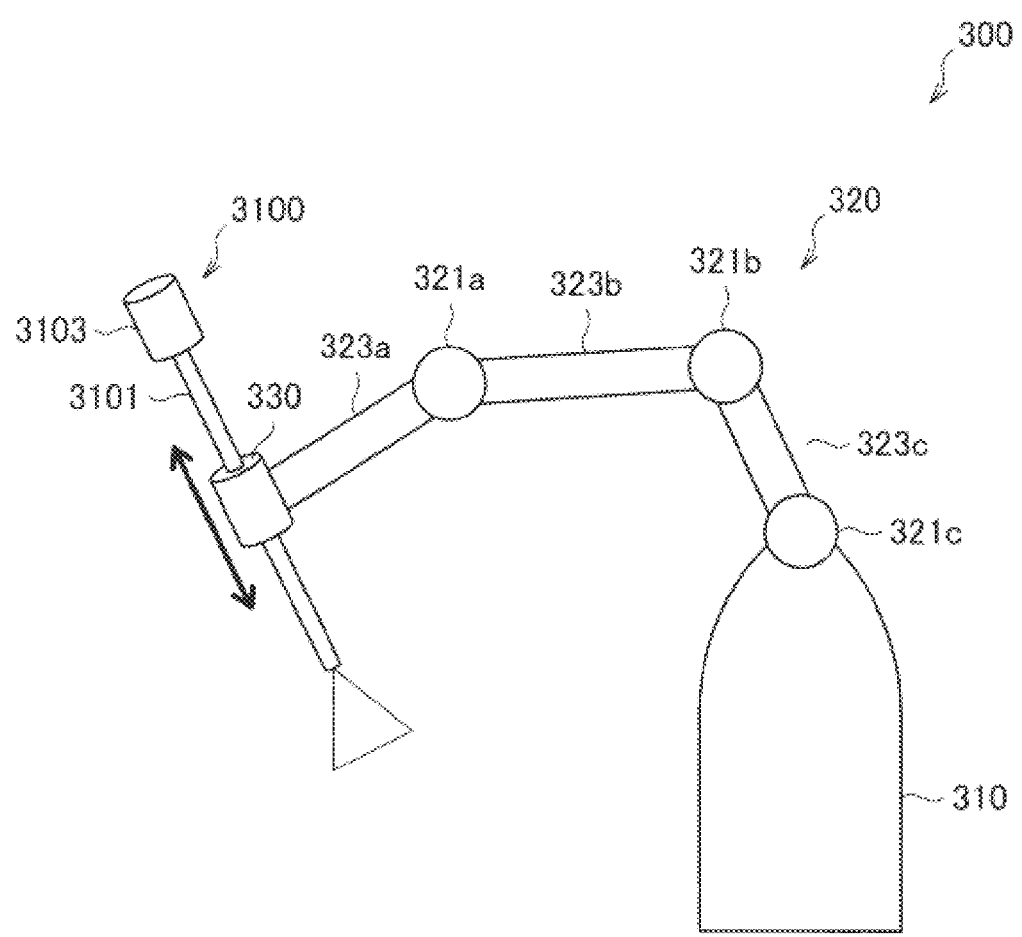

[Fig. 15]
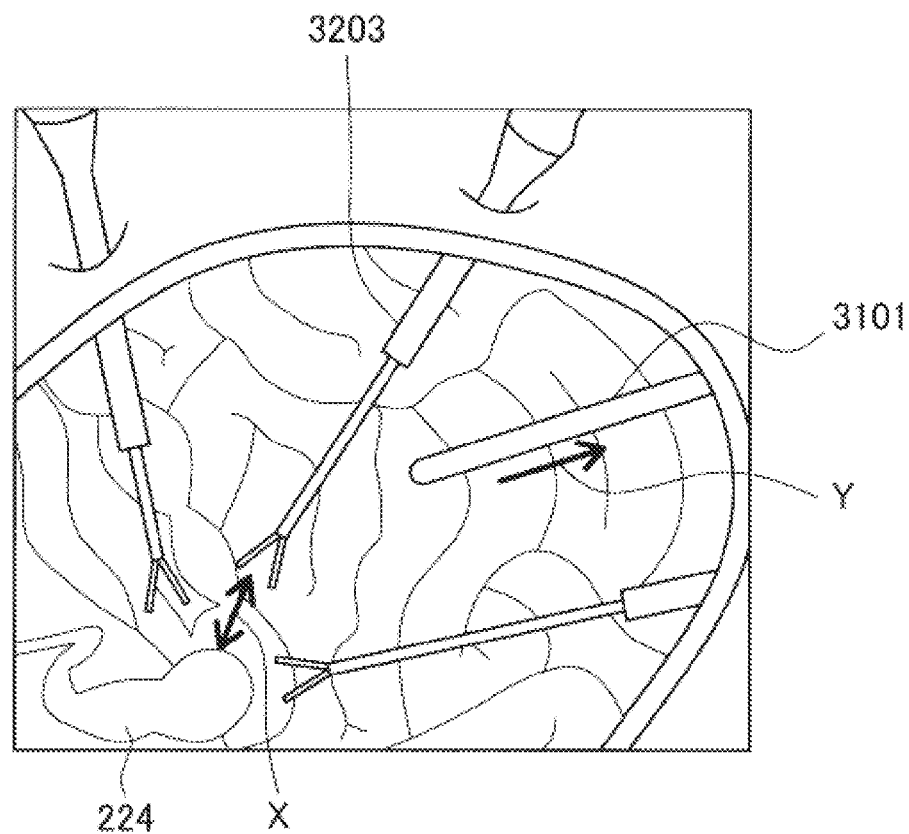
[Fig. 16]
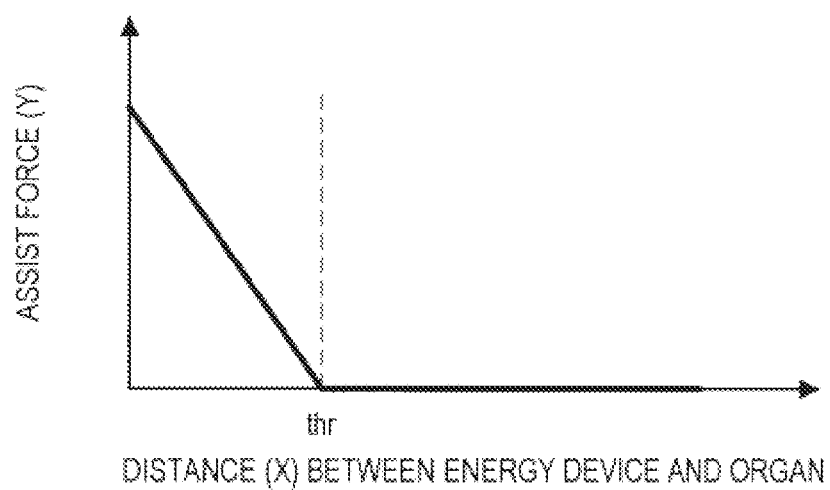

[Fig. 17]
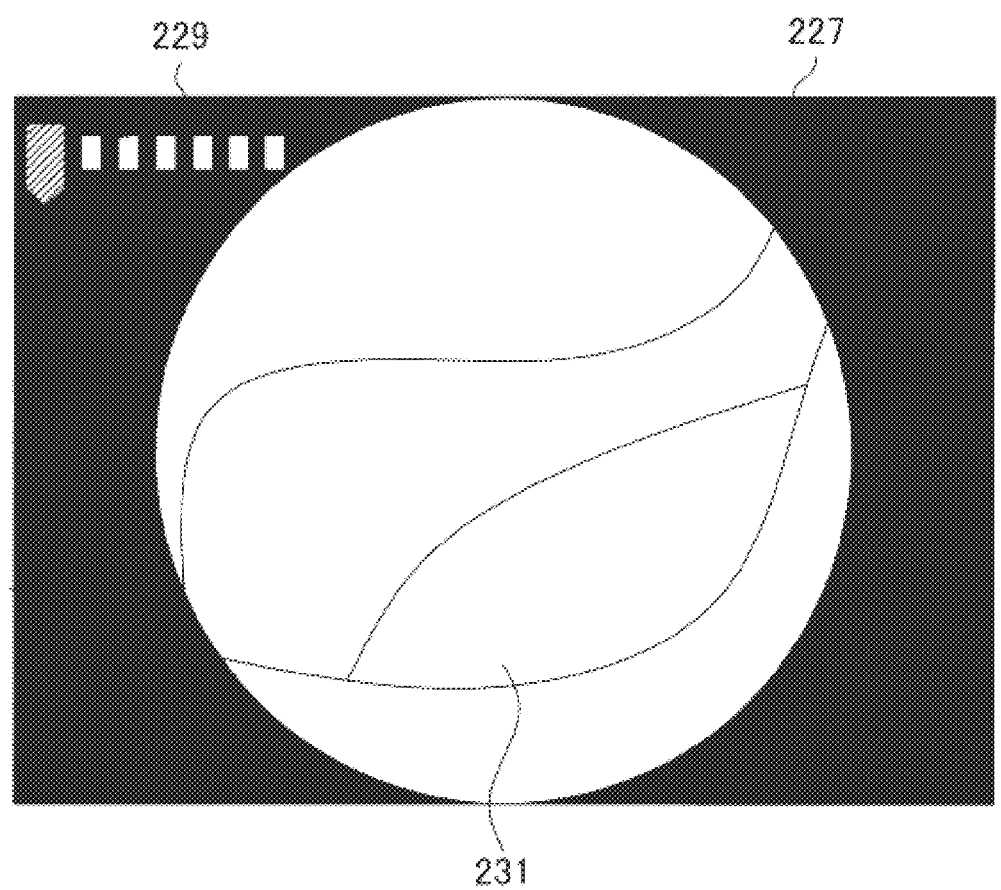

IMAGE PROCESSING DEVICE, ENDOSCOPIC SURGERY SYSTEM, AND IMAGE PROCESSING METHOD

CROSS REFERENCE TO RELATED APPLICATIONS

This application is a U.S. National Phase of International Patent Application No. PCT/JP2017/006341 filed on Feb. 21, 2017, which claims priority benefit of Japanese Patent Application No. JP 2016-045440 filed in the Japan Patent Office on Mar. 9, 2016. Each of the above-referenced applications is hereby incorporated herein by reference in its entirety.

TECHNICAL FIELD

The present disclosure relates to an image processing device, an endoscopic surgery system, and an image processing method.

BACKGROUND ART

In an endoscopic surgical operation, a member of a medical staff such as an operator (a doctor) inserts a lens barrel of an endoscope into a body cavity of a patient to project a captured image obtained from the endoscope onto a display device, and manipulates a treatment device to perform various kinds of treatment such as excision of a lesion viewing this display. Thus, the image should be provided to the medical staff more stably in order to help them execute the surgical operation more safely and more smoothly.

As a technology for stably providing an image, for example, PTL 1 discloses a technology in which a position of the leading end of a treatment instrument in a body cavity of a patient is detected, movement of a specific part of the treatment instrument is tracked in a captured image photographed by an endoscope to cut out only an area near the specific part of the treatment instrument, and a display device displays the image. According to the technology, the image near the specific part of the treatment instrument is constantly displayed, with no necessity for an endoscopist to manipulate the endoscope with hands to track movements of the treatment instrument, and thus the image can be provided to the medical staff more stably.

In addition, there are cases in which mist is generated from a cauterized biological tissue when treatment is performed using an energy device during a surgical operation. When mist is generated while an observation target site including the treatment site is photographed, there are concerns of an endoscope equipped with an auto-focus (AF) function performing an erroneous operation of AF due to the mist which lowers its contrast, and of a vivid image of the treatment site not being obtained. On the other hand, PTL 2 discloses a technology of stopping a focusing operation of an endoscope equipped with an AF function when generation of mist is detected. According to this technology, even when mist is generated, an image obtained before the generation of mist whose focus is on a treatment site is displayed as it is with no erroneous operation of AF, and thus the image can be provided to medical staff more stably.

CITATION LIST

Patent Literature

[PTL 1]
JP H8-164148A
[PTL 2]
JP 2015-136470A

SUMMARY

Technical Problem

Here, when mist is generated as described above or when body fluid such as blood is scattered due to treatment in an endoscopic surgical operation, if an objective lens of a lens barrel is contaminated by the mist and/or the body fluid, there is a concern of an observation target site not being clearly photographed. Thus, in the case of generation of mist and/or scattered body fluid, the lens barrel can be moved during photographing in order to avoid such substances. Or, the lens barrel may be moved likewise, for example, to secure a work space for performing treatment using other treatment instruments. As described above, it may be necessary to move a lens barrel during photographing in an endoscopic surgical operation for various reasons.

If an image can be provided to a medical staff more stably even when a lens barrel is moved as described above, it will help the medical staff perform a smooth operation, and thus there are possibilities of safety of surgical operations improving and operation times being shortened.

A technology for providing a medical staff with an image more stably during an endoscopic surgical operation when a lens barrel of the endoscope is moved has been demanded with the above-described circumstances taken into account. Thus, embodiments of the present disclosure proposes a novel and improved image processing device, endoscopic surgery system, and image processing method that enable an image to be provided to a member of a medical staff such as an operator more stably.

Solution to Problem

According to an embodiment of the present disclosure, there is provided an image processing device including circuitry configured to generate image data from an image captured by an endoscope of an inside of a body of a patient, and in response to the endoscope being moved during image capture, the circuitry generates the image data so that a display range of a corresponding image displayed on a display device does not substantially change.

According to an embodiment of the present disclosure, there is provided An endoscopic surgery system including: an image processing device including circuitry configured to generate image data from an image captured by an endoscope of an inside of a body of a patient, and in response to the endoscope being moved during image capture, the circuitry generates the image data so that a display range of a corresponding image displayed on an external display device does not substantially change; and an arm control device that controls driving of a supporting device that supports the endoscope with an arm unit, and moves a lens barrel of the endoscope, in response to a predetermined retraction condition being satisfied, the circuitry is configured to issue an instruction to the arm control device to execute a retraction operation to move the lens barrel in a retraction direction, which is an optical axis direction of an objective lens and in which the lens barrel is moved away from an observation target site, and in response to a predetermined return condition being satisfied, the circuitry is configured to issue an instruction to the arm control device to execute a return operation to move the lens barrel in a return direction, which is the optical axis direction of the objective lens and in which the lens barrel comes near the observation target site, when a predetermined return condition is satisfied.

According to an embodiment of the present disclosure, there is provided An image processing method including generating with circuitry image data from an image captured by an endoscope of an inside of a body of a patient, and in response to the endoscope being moved during image capture, the circuitry generating the image data so that a display range of a corresponding image displayed on an external display device does not substantially change.

According to the embodiments of the present disclosure, when a lens barrel of an endoscope is moved in an optical axis direction of an objective lens during photographing, image data for displaying a captured image on a display device is generated such that a display range in the captured image that is a range expressed in a display image displayed on the display device does not change, during and after the movement, from a display range before the movement. Thus, a substantially constant image can be stably provided to a member of a medical staff such as an operator viewing the display of the display device even while the lens barrel is being moved.

Advantageous Effects of Invention

According to the embodiments of the present disclosure described above, it is possible to provide an image to a member of a medical staff such as an operator more stably. Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 1 is a diagram showing an example of a configuration of an endoscopic surgery system according to a first embodiment.

FIG. 2 is a block diagram showing an example of a configuration of an image processing system according to the first embodiment.

FIGS. 3A and 3B are diagrams for describing movement of a lens barrel during a retraction operation.

FIG. 4 is a diagram schematically showing relations of photographing ranges, captured images, and display images before and during retraction of the lens barrel.

FIG. 5 is a flowchart showing an example of a process procedure of an image processing method according to the first embodiment.

FIG. 6 is a block diagram showing an example of a configuration of an image processing system according to a second embodiment.

FIG. 7 is a flowchart showing an example of a process procedure of an image processing method executed in an image processing system according to a third embodiment.

FIGS. 8A and 8B are diagrams for describing a method of detecting generation of mist according to a modified example in which a mist detection target area is set in a part inside a captured image.

FIGS. 9A and 9B are diagrams for describing a modified example in which a distance between a treatment instrument and a treatment site is a retraction condition and a return condition.

FIG. 10 is a diagram for describing a point of interest of an energy device.

FIG. 11 is a block diagram showing a configuration of an image processing system according to a modified example in which states of an energy device are used as a retraction condition and a return condition.

FIG. 12 is a diagram showing a state in which an operator uses an energy device.

FIG. 13 is a block diagram showing a configuration of an image processing system according to a modified example in which an instruction of a user is set as a retraction condition and a return condition.

FIG. 14 is a diagram schematically showing an example of another configuration of a support arm device.

FIG. 15 is a diagram for describing assist force related to a semi-automatic retracting operation and return operation.

FIG. 16 is a diagram for describing assist force related to a semi-automatic retracting operation and return operation.

FIG. 17 is a diagram showing an example of display of a distance between a leading end of a lens barrel and an observation target site on a display screen.

DESCRIPTION OF EMBODIMENTS

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Note that description will be provided in the following order.
1. First embodiment
1-1. Configuration of endoscopic surgery system
1-2. Configuration of image processing system
1-3. Image processing method
2. Second embodiment
3. Third embodiment
4. Modified examples
4-1. Other method for detection of mist based on captured image
4-2. Other examples of retraction condition and return condition
4-2-1. Distance between treatment instrument and treatment site
4-2-2. State of energy device
4-2-3. Detection of movement of leading end of energy device
4-2-4. Instruction from user
4-2-5. Distance between leading end of lens barrel of endoscope and treatment instrument
4-3. Other example of configuration of support arm device
4-4. Semi-automatization of retraction operation and return operation
5. Supplement Note that, as exemplary embodiments of the present disclosure, examples in which the present technology is applied to an endoscopic surgery system will be described below. In addition, in the following description, a "user" is assumed to mean at least one member of a medical staff using the endoscopic surgery system (a doctor who is performing treatment on a treatment site (an operator), a doctor who is manipulating an endoscope (an endoscopist), an assistant, and the like). The user will be described as an operator, an endoscopist, or the like when it is particularly necessary to distinguish them.

In addition, sizes of some constituent members are in some cases expressed to be enlarged in the drawings shown below for description, and relative sizes of the respective constituent members illustrated in the drawings do not necessarily express the accurate size relations of the actual constituent members.

1. First Embodiment

1-1. Configuration of Endoscopic Surgery System

A configuration of an endoscopic surgery system to which an image processing system according to a first embodiment of the present disclosure can be applied will be described with reference to FIG. 1. FIG. 1 is a diagram showing an example of the configuration of the endoscopic surgery system 3000 according to the first embodiment. FIG. 1 illustrates a state in which an operator (a doctor) 3501 is conducting a surgical operation on a patient 3505 lying on a patient bed 3503, using the endoscopic surgery system 3000. As illustrated, the endoscopic surgery system 3000 is constituted by an endoscope 3100, other surgical instruments 3200, a support arm device 3300 that supports the endoscope 3100, and a cart 3400 on which various devices for the endoscopic surgical operation are mounted.

In the endoscopic surgery, an abdominal wall is punctured with a plurality of tubular opening tools called trocars 3207a to 3207d, instead of cutting the abdominal wall for an abdominal section. Then, a lens barrel 3101 of the endoscope 3100 and the other surgical instruments 3200 are inserted into the body cavity of the patient 3505 through the trocars 3207a to 3207d. In the illustrated example, as the other surgical instruments 3200, a pneumoperitoneum tube 3201, an energy device 3203, and a forceps 3205 are inserted into the body cavity of the patient 3505. In addition, the energy device 3203 is a treatment instrument for performing incision and dissection of tissue, suturing of a blood vessel, and the like using a high-frequency current or ultrasonic vibration. However, the illustrated surgical instruments 3200 are merely examples, and as the surgical instruments 3200, various surgical instruments generally used in endoscopic surgical operations, for example, tweezers, retractors, and the like, may be used. Note that, among the surgical instruments, ones that perform various kinds of treatment such as excision, holding, and supporting with respect to biological tissue (viscera, blood vessels, etc.) inside the body cavity of the patient will also be referred to as treatment instruments in the following description. Among those exemplified above, the energy device 3203, the forceps 3205, tweezers, and retractors correspond to treatment instruments.

An image of an operation site inside the body cavity of the patient 3505 photographed by the endoscope 3100 is displayed on a display device 3403. The operator 3501 performs treatment, for example, excising a body tissue corresponding to a lesion, using the energy device 3203 and forceps 3205 while viewing the image of the operation site displayed on the display device 3403 in real time. Note that, although not shown in the drawing, the pneumoperitoneum tube 3201, the energy device 3203, and the forceps 3205 are supported and manipulated by the operator 3501, an assistant, etc. during the surgical operation.

Support Arm Device

The support arm device 3300 is provided with an arm unit 3303 stretching from a base unit 3301. In the illustrated example, the arm unit 3303 is constituted by joints 3305a, 3305b, and 3305c, and links 3307a and 3307b, and is driven under control of an arm control device 3407. The endoscope 3100 is supported by the arm unit 3303, and thus its position and attitude are controlled. Accordingly, stable fixation of a position of the endoscope 3100 can be realized.

However, FIG. 1 shows a simplified configuration of the arm unit 3303 for simplicity. In order for the arm unit 3303 to have a desired degree of freedom in practice, shapes, numbers, and disposition of the joints 3305a to 3305c and the links 3307a and 3307b, and directions of rotation axes of the joints 3305a to 3305c can be appropriately set. For example, the arm unit 3303 can have an appropriate degree of freedom equal to or higher than 6 degrees of freedom. Accordingly, since the endoscope 3100 can be freely moved within a movable range of the arm unit 3303, it is possible to insert the lens barrel 3101 of the endoscope 3100 into the body cavity of the patient 3505 from a desired direction.

Actuators are provided in the joints 3305a to 3305c, and thus the joints 3305a to 3305c are rotatable around predetermined rotation axes as they are driven by the actuators. Since driving of these actuators is controlled by the arm control device 3407 to be described below in a coordinated manner, rotation angles of the respective joints 3305a to 3305c are appropriately controlled, and thereby attitudes of the arm unit 3303 are controlled. Positions and attitudes of the endoscope 3100 are controlled accordingly.

Specifically, the actuators provided in the joints 3305a to 3305c include various sensors for detecting states of the joints such as an encoder that detects rotation angles of the respective joints, a torque sensor that detects torque applied to the respective joints, and the like. Detection values of these sensors are transmitted to the arm control device 3407. The arm control device 3407 has an internal model in which geometric states and mechanical states of the arm unit 3303 are expressed with internal coordinates of the support arm device 3300, and based on the internal model and detection values of the sensors, current states of the joints 3305a to 3305c, i.e., a current state of the arm unit 3303 (including a position, a posture, a speed, etc.), can be ascertained. Based on the ascertained state of the arm unit 3303, the arm control device 3407 calculates driving control amounts (for example, rotation angles, or driving torque) of the respective joints corresponding to manipulation input from the user with regard to an operation of the arm unit 3303, and drives the respective joints according to the driving control amounts.

For example, when the user appropriately performs manipulation input via an input device 3409 (including a foot switch 3419), the arm control device 3407 appropriately controls driving of the arm unit 3303 according to the manipulation input, and thereby a position and an attitude of the endoscope 3100 may be controlled. Alternatively, the arm unit 3303 may be manipulated through gestures of the user, or the like. Alternatively, the arm unit 3303 may be manipulated through a so-called master-slave scheme. In this case, the arm unit 3303 can be manipulated remotely by the user via the input device 3409 installed at a place away from an operation room.

Note that a driving scheme of the arm unit 3303 is not limited in the first embodiment, and the arm control device 3407 can control driving of the arm unit 3303 using any of various known control schemes, such as force control or position control. In this case, when force control is applied, the arm control device 3407 can perform so-called power-assist control to drive the actuators of the respective joints 3305a to 3305c according to manipulation performed by the endoscopist who manipulates the endoscope 3100 making direct contact with the arm unit 3303 or the endoscope 3100 (hereinafter, also referred to as direct manipulation) so that the arm unit 3303 is smoothly moved according to external force in the direct manipulation. Accordingly, when the endoscopist moves the arm unit 3303 while in direct contact with the arm unit 3303, the arm unit 3303 can be moved with relatively light force. Thus, it is possible to more intuitively move the endoscope 3100 with simpler manipulation, and thus convenience for the endoscopist can be enhanced.

Endoscope

The endoscope 3100 is constituted by the lens barrel 3101 whose area in a predetermined length from its leading end is inserted into the body cavity of the patient 3505, and a camera head 3103 which is connected with a base end of the lens barrel 3101. In the first embodiment, the endoscope 3100 is a so-called hard mirror with the hard lens barrel 3101.

An opening in which an objective lens is framed is provided at the leading end of the lens barrel 3101. In the first embodiment, the endoscope 3100 is a so-called direct view mirror in which the objective lens is provided so that its optical axis is in parallel with the stretching direction of the lens barrel 3101. The endoscope 3100 is connected with a light source device 3405, and light generated by the light source device 3405 is guided to the leading end of the lens barrel 3101 by a light guide stretching inside the lens barrel, and radiated toward an observation target site inside the body cavity of the patient 3505 through the objective lens. Reflected light (observation light) from the observation target site is led to the camera head 3103 via the objective lens and a relay optical system provided inside the lens barrel 3101.

An optical system and an image sensor are provided inside the camera head 3103, and the observation light is concentrated on the image sensor via the optical system. The image sensor photoelectrically converts the observation light, and thereby generates an electric signal corresponding to the observation light, i.e., an image signal corresponding to the observation image. The image signal is transmitted to a camera control unit (CCU) 3401 as raw data. Note that a mechanism which adjusts magnification and focal length (focus) by appropriately driving the optical system is mounted in the camera head 3103.

Note that the camera head 3103 may be provided with a plurality of image sensors in order to support, for example, stereoscopic views (3D display), and the like. That is, a stereo camera may be mounted in the endoscope 3100. In this case, a plurality of relay optical systems may be provided inside the lens barrel 3101 in order to guide observation light to the plurality of image sensors.

Various Devices Mounted in Cart

The CCU 3401 is constituted by a central processing unit (CPU), a graphics processing unit (GPU), and the like to control overall operations of the endoscope 3100, the display device 3403, and the arm control device 3407. The CCU 3401 corresponds to an image processing device according to an embodiment of the present disclosure. Specifically, the CCU 3401 performs various kinds of image processing on the image signal received from the camera head 3103 for causing an image based on the image signal to be displayed on the display device 3403, for example, development processing (demosaicing), enlargement processing (electronic zoom processing), and the like. Consequently, the CCU 3401 generates image data for displaying a captured image photographed by the endoscope 3100 on the display device 3403. The CCU 3401 transmits the image signal that has undergone the various kinds of image processing (i.e., the generated image data) to the display device 3403.

In addition, the CCU 3401 transmits a control signal to the camera head 3103 to control its driving. The control signal can include information regarding imaging conditions such as magnification and focus.

Furthermore, when a predetermined condition is satisfied, the CCU 3401 transmits an instruction to retract the lens barrel 3101 of the endoscope 3100 from its current position to the arm control device 3407 along with information regarding a retraction movement amount at that time. Based on that instruction, the arm control device 3407 drives the arm unit 3303 so that the lens barrel 3101 is moved the retraction movement amount away from the observation target site. At this time, the arm control device 3407 moves the lens barrel 3101 in the optical axis direction of the objective lens provided at its leading end, i.e., the stretching direction of the lens barrel 3101.

In the first embodiment, the CCU 3401 generates the above-described image data such that a display range in the captured image by the endoscope 3100 that is a range expressed in a display image displayed on the display device 3403 does not change, while the lens barrel 3101 is moving or after it moves according to the retraction instruction, from a display range before the movement. Accordingly, since the display device 3403 constantly displays the same range of the inside of the observation target site of the captured image by the endoscope 3100 during and after the movement of the lens barrel 3101, the operator 3501 is provided with substantially the same display more stably, regardless of the movement of the lens barrel 3101.

Note that the movement of the lens barrel 3101 of the endoscope 3100 and the image processing following the movement performed by the CCU 3401 and the arm control device 3407 described above will be described again in detail in (1-2. Configuration of image processing system) below.

The display device 3403 displays the image based on the image data generated by the CCU 3401 under control of the CCU 3401. When the endoscope 3100 supports high-resolution photographing, for example, 4K (3840, the number of horizontal pixels×2160, the number of vertical pixels) or 8K (7680, the number of horizontal pixels×4320, the number of vertical pixels), and/or supports 3D display, a device that enables high-resolution display and/or 3D display can be used as the display device 3403 to support the resolutions. When a device having a 55-inch screen or larger is used as the display device 3403 to support the high-resolution photographing such as 4K or 8K, a deeper feeling of immersion can be obtained. In addition, a plurality of display devices 3403 with different resolutions and sizes may be provided according to their purposes.

The light source device 3405 is a light source, for example, a light emitting diode (LED), etc., for supplying radiation light to the endoscope 3100 when the operation site is photographed.

The arm control device 3407 is constituted by a processor, for example, a CPU, etc., to control driving of the arm unit 3303 of the support arm device 3300 according to a predetermined control scheme when it operates according to a predetermined program.

An input device 3409 is an input interface for the endoscopic surgery system 3000. A user can perform input of various kinds of information and input of instructions to the endoscopic surgery system 3000 through the input device 3409. For example, a user inputs various kinds of information regarding the surgical operation, such as body information of the patient or an operation method of the surgical operation, through the input device 3409. In addition, for example, a user inputs an instruction to drive the arm unit 3303, an instruction to change an imaging condition (a type of radiation light, magnification, focus, or the like) of the endoscope 3100, or an instruction to drive the energy device 3203 through the input device 3409.

Kinds of the input device 3409 are not limited, and a variety of known input devices may be used as the input device 3409. As the input device 3409, for example, a mouse, a keyboard, a touch panel, a switch, the foot switch 3419, and/or a lever can be applied. When a touch panel is used as the input device 3409, the touch panel may be provided on a display surface of the display device 3403.

Alternatively, the input device 3409 may include a device worn by a user, for example, a glasses-type wearable device, a head mounted display (HMD), or the like, and may perform various kinds of input according to a gesture or a line of sight of the user detected by the device. In addition, the input device 3409 may include a camera that can detect motions of a user, and may perform various kinds of input according to a gesture or a line of sight of the user detected from a video captured by the camera. Furthermore, the input device 3409 may include a microphone that can collect voice of the user, and may perform various kinds of input using voice through the microphone. In this manner, when the input device 3409 is capable of inputting various kinds of information with no contact, in particular, the user (for example, the operator 3501) particularly located in a clean area can manipulate an apparatus located in an unclean area with no contact. In addition, since the user can manipulate such an apparatus without removing his or her hand from a surgical instrument that he or she is holding, user convenience is enhanced.

A treatment instrument control device 3411 controls driving of the energy device 3203 which is used for cauterization or incision of tissues, or suturing of blood vessels. A pneumoperitoneum device 3413 sends a gas into the body cavity via the pneumoperitoneum tube 3201 to inflate the body cavity of the patient 3505, for the purpose of securing a visual field of the endoscope 3100 and securing a work space of the operator. A recorder 3415 is a device that can record various kinds of information regarding the surgical operation. A printer 3417 is a device that can print various kinds of information regarding the surgical operation in various forms such as text, images, and graphs.

The configuration of the endoscopic surgery system 3000 has been described above.

1-2. Configuration of Image Processing System

A configuration of an image processing system 1 according to the first embodiment to be applied to the above-described endoscopic surgery system 3000 will be described with reference to FIG. 2. FIG. 2 is a block diagram showing an example of the configuration of the image processing system 1 according to the first embodiment. The image processing system 1 controls the display image displayed on the display device 3403 when the endoscope 3100 is moved during the surgical operation. Note that FIG. 2 illustrates a configuration related only to the image processing system 1 extracted from the above-described endoscopic surgery system 3000. The configuration of the image processing system 1 will be described below with reference to the configuration of the endoscopic surgery system 3000 shown in FIG. 1 as well.

Referring to FIG. 2, the image processing system 1 includes the endoscope 3100, the CCU 3401, the arm control device 3407, and the arm unit 3303 of the support arm device 3300.

An image sensor 111 and a focus adjustment mechanism 112 are mounted in the endoscope 3100 (more precisely, in the camera head 3103 of the endoscope 3100) as described above. Image signals obtained by the image sensor 111 are transmitted to the CCU 3401 at a predetermined interval corresponding to a frame rate during a surgical operation when necessary.

The CCU 3401 has a movement control unit 121, an image processing unit 122, and a focus control unit 123 as its functions. These functions can be realized when a processor constituting the CCU 3401 operates according to a predetermined program.

The image processing unit 122 performs various kinds of image processing on an image signal obtained by the image sensor 111, and thereby generates image data related to a captured image. In addition, based on the image data related to the captured image, the image processing unit 122 generates image data for output. The image data for output refers to image data specifically processed in a form that various kinds of data output devices such as the display device 3403, the recorder 3415, and the printer 3417 of the above-described endoscopic surgery system 3000 can process. In the present embodiment, the image processing unit 122 generates image data related to a display image to be displayed on the display device 3403 based on the image data related to the captured image.

Here, in the present specification, a captured image refers to an image having magnification, angle of view, focus, and the like decided according to hardware of the imaging mechanism of the endoscope 3100 such as the image sensor 111 and the optical system provided in its preceding stage. On the other hand, a display image refers to an image actually displayed on the display device 3403. A display image may refer to a captured image itself. Alternatively, a display image may be an image obtained by performing predetermined processing on a captured image, by cutting a partial region out from a captured image, enlarging a partial region of a captured image using an electronic zoom function, or the like. In other words, the image processing unit 122 generates image data related to a display image by performing various kinds of processing on the image data related to the captured image or performing no processing thereon.

At normal times, i.e., when the movement control unit 121 to be described below does not control movement of the lens barrel 3101 during a surgical operation, the type of image data related to a display image to be generated by the image processing unit 122 can be appropriately set by a user. That is, at normal times, the image processing unit 122 generates image data related to a display image according to a condition appropriately set by the user (cutting-out of a captured image, enlargement using electronic zoom, or the like). Then, the generated image data is transmitted to the display device 3403 and then displayed. The operator 3501 manipulates a treatment instrument while observing the state of the treatment site in this display image to perform various kinds of treatment for the treatment site.

When a predetermined condition is satisfied, the movement control unit 121 controls movement of the lens barrel 3101 by issuing an instruction to move the lens barrel 3101 of the endoscope 3100 to the arm control device 3407. Specifically, when a predetermined retraction condition is satisfied, the movement control unit 121 moves the lens barrel 3101 so that the lens barrel 3101 is moved away from the observation target site. In addition, when a predetermined return condition is satisfied, the movement control unit 121 moves the lens barrel 3101 so that the lens barrel 3101 returns to the position before retraction (i.e., the lens barrel 3101 comes near the observation target site). Note that the movement direction of the lens barrel 3101 at the time of the retraction and return operations is the optical axis direction of the objective lens provided in the lens barrel 3101, i.e., the stretching direction of the lens barrel 3101.

In the first embodiment, the retraction condition is that generation of mist caused by cauterizing a body tissue using the energy device 3203 is detected. In addition, the return condition is that disappearance of the mist is detected. Specifically, the movement control unit 121 detects generation and disappearance of mist based on the image data related to the captured image generated by the image processing unit 122. Note that, since any of various known methods for an image recognition process may be used as a specific method of detecting generation and disappearance of mist based on image data, detailed description thereof will be omitted here. For example, the method disclosed in PTL 2 (JP 2015-136470A) described above can be favorably used in detecting generation and disappearance of mist based on image data. In the method disclosed in PTL 2, an evaluation value indicating a temporal change in luminance and an evaluation value indicating a temporal change in saturation of a captured image, and an evaluation value indicating a temporal change in a dynamic range are calculated, and based on these evaluation values, generation and disappearance of mist are detected.

When generation of mist is detected, the movement control unit 121 decides a retraction movement amount which is a movement amount of the lens barrel 3101 at the time of a retraction operation, and transmits an instruction to perform a retraction operation and information regarding the retraction movement amount to the arm control device 3407. In the first embodiment, a certain value set in advance by the user is used as the retraction movement amount. For example, the retraction movement amount may be appropriately set to a value at which the generated mist is not likely to affect the captured image of the endoscope 3100.

In addition, when disappearance of the mist is detected, the movement control unit 121 decides a return movement amount that is a movement amount of the lens barrel 3101 at the time of return, and transmits an instruction to perform a return operation and information regarding the return movement amount to the arm control device 3407. At this time, the return movement amount is set to the same value as the retraction movement amount.

The focus control unit 123 controls driving of the focus adjustment mechanism 112 of the endoscope 3100 so that the observation target site is in focus at all times during and after the movement of the lens barrel 3101. Accordingly, the captured image photographed before retraction whose focus is on the observation target site is obtained constantly in the series of movements in the retraction and return operations of the lens barrel 3101.

The arm control device 3407 has an actuator driving control unit 131 as a function. The function can be realized when a processor constituting the arm control device 3407 operates according to a predetermined program.

Actuators 141 are provided in the respective joints of the arm unit 3303 of the support arm device 3300. The actuator driving control unit 131 drives the actuators 141 provided in the respective joints of the arm unit 3303 in a coordinated manner according to the instruction from the movement control unit 121 in various control schemes and thereby causes the arm unit 3303 to operate, and thus the lens barrel 3101 is caused to perform the retraction operation and the return operation. Note that FIG. 2 expresses that the endoscope 3100 is physically supported by the arm unit 3303 by linking both blocks with a dashed-lined arrow.

The arm control device 3407 ascertains the actual movement amounts of the lens barrel 3101 at the time of the retraction operation and the return operation based on detection values of sensors provided in the respective joints of the arm unit 3303 when necessary. During the retraction operation and the return operation, the arm control device 3407 transmits information regarding the movement amounts of the lens barrel 3101 to the CCU 3401 when necessary.

In the first embodiment, while the retraction operation and return operation of the lens barrel 3101 are being performed, the image processing unit 122 generates image data based on a display image different from one at normal times. Then, this generated image data is transmitted to the display device 3403 and displayed thereon. Specifically, the image processing unit 122 generates the image data such that a display range in the image captured by the endoscope 3100 that is a range expressed in a display image displayed on the display device 3403 does not change, during or after the movement of the lens barrel 3101, from a display range before the movement.

Processing performed by the image processing unit 122 at the time of the retraction operation and the return operation of the lens barrel 3101 will be described in detail with reference to FIGS. 3A, 3B, and 4. Here, image processing will be described in detail exemplifying a case of a retraction operation.

FIGS. 3A and 3B are diagrams for describing movement of a lens barrel during a retraction operation. FIG. 3A shows a state before retraction. In this state, treatment is performed using the energy device 3203, and when mist 201 is generated, the generation of the mist 201 is detected by the movement control unit 121 of the CCU 3401 as described above, and an instruction to perform a retraction operation is issued. FIG. 3B shows a state at the time of retraction. According to that instruction, the actuator driving control unit 131 of the arm control device 3407 moves the lens barrel 3101 to retract in the optical axis direction of the objective lens as shown in FIG. 3B.

FIG. 4 is a diagram schematically showing relations of photographing ranges, captured images, and display images before and during the retraction operation of the lens barrel 3101. The left column of the FIG. 4 schematically shows the photographing range, the captured image, and the display image before the retraction operation, and the right column thereof schematically shows the photographing range, the captured image, and the display image during the retraction operation.

A state of the inside of a given photographing range 203 is photographed as a captured image 205 at a position of the lens barrel 3101 before the retraction operation (i.e., at normal times) as shown in FIG. 4. In addition, if the user performs no particular setting such as cutting-out or electronic zoom, substantially the same image as this captured image 205 is displayed as a display image 207.

On the other hand, as the lens barrel 3101 is moved away from the observation target site during the retraction operation, a photographing range 209 in that case becomes greater than the photographing range 203 before the retraction operation as illustrated. In FIG. 4, the photographing range 203 before the retraction operation is indicated with a two-dot chain line in the photographing range 209 during the retraction operation for the sake of convenience in description. In this case, since appearance of this photographing range 209 is obtained as a captured image 211, an image of a wider range including the captured image 205 before the retraction operation is obtained as a captured image 211 as illustrated. In this case, if this captured image 211 is projected as a display image without change, like before the retraction operation, the display image changes as if display of the treatment site were gradually decreasing, and thus the operator 3501 should stop performing treatment during that time, which makes it difficult to smoothly execute the surgical operation.

Thus, in the first embodiment, the image processing unit 122 cuts out an area 213 corresponding to the display range before the retraction operation included in the captured image 211 acquired during the retraction operation of the lens barrel 3101, enlarges the area 213 using the electronic zoom function, and thereby generates the image data related to the display image. Specifically, since the lens barrel 3101 is set to be moved in the optical axis direction of the objective lens during the retraction operation in the first embodiment as described above, the image processing unit 122 may gradually reduce the size of the cut-out area 213 according to the movement amount of the lens barrel 3101, with the center of the cut-out area 213 fixed to the center of the captured image 211. Note that the movement amount of the lens barrel 3101 may be calculated based on information regarding the position of the lens barrel 3101 before the retraction operation transmitted from the arm control device 3407 and information regarding the current position of the lens barrel 3101. Accordingly, while a display image 215 showing the retraction can have a slightly deteriorating quality due to the electronic zoom, an image substantially similar to the display image 207 before the retraction is obtained.

Although the image processing performed at the time of the retraction operation has been described above exemplifying the case of the retraction operation, the image processing unit 122 executes similar processes at the time of a return operation. Specifically, the image processing unit 122 cuts out an area corresponding to the display range before the retraction operation included in a captured image acquired during the return operation of the lens barrel 3101, enlarges the area using the electronic zoom function, and thereby generates image data related to a display image. At this time, during the retraction operation, the image processing unit 122 may gradually increase the size of the cut-out area according to a movement amount of the lens barrel 3101 with the center of the cut-out area fixed to the center of the captured image.

In the first embodiment, since the above-described image processing is performed, the image to be provided to the operator 3501 hardly changes even if the lens barrel 3101 is moved according to the retraction operation or the return operation. That is, even if the lens barrel 3101 is moved during the surgical operation, the image can be provided to the operator more stably, and thus safety of the surgical operation can be improved, and the surgical operation can be performed more smoothly. In addition, it is possible to further shorten an operation time.

The configuration of the image processing system according to the first embodiment has been described above. Note that, although the retraction condition and the return condition are set to detection of generation of mist and detection of disappearance of the mist respectively in the example of the configuration described above, the present embodiment is not limited thereto. For example, a retraction condition and a return condition may be set with regard to scattering of body fluid such as blood caused by treatment using a treatment instrument, instead of or along with generation of mist. In addition, although the image processing unit 122 has been described as generating the image data related to the display image displayed on the display device 3403 above, the first embodiment is not limited thereto. In the first embodiment, the image processing unit 122 can generate image data for output with respect to another data output device like the recorder 3415 or the printer 3417 as described above. In this case, the image processing unit 122 can generate the image data for output according to each data output device such that a display range in the image captured by the endoscope 3100 that is a range expressed in a display image displayed on the display device 3403 does not change, during or after the movement of the lens barrel 3101, from a display range before the movement. Consequently, the image processing unit 122 may not necessarily create image data to be displayed on the display device 3403, and may create image data to be recorded by a recording device such as the recorder 3415, or image data to be printed by a printing device such as the printer 3417.

Here, when treatment is performed on a treatment site using a treatment instrument in a general endoscopic surgical operation, mist is generated or body fluid such as blood is scattered as described above. When photographing is performed by bringing the lens barrel 3101 of the endoscope 3100 relatively close to an observation target site including the treatment site, if generation of mist and scattering of body fluid occur as described above, such mist and/or body fluid contaminates the objective lens of the lens barrel 3101, and thus it may not be possible to vividly observe or photograph the observation target site.

With regard to this, when the objective lens of the lens barrel 3101 is contaminated by mist and/or body fluid during the surgical operation, a method of taking the lens barrel 3101 out of the body cavity of the patient for a while, cleaning it, inserting the lens barrel 3101 back into the body cavity of the patient, and then resuming photographing of the observation target site is adopted.

In this method, however, photographing is of course stopped while the lens barrel 3101 is taken out, and thus it is not possible to check states of other treatment instruments inserted into the body cavity during that time, which may cause a hazard. In addition, when the lens barrel 3101 is inserted again, it is necessary to reproduce substantially the same observation state as before photographing was stopped. Thus, the work imposes an increasing burden on the endoscopist, which results in an increase of an operation time, and therefore burdens on the operator 3501 and the patient 3505 increase as well. Furthermore, the very work of taking out the lens barrel 3101 for a while and then inserting it again can be a burden on the endoscopist and the patient 3505. In addition, since it is difficult to place the lens barrel 3101 at the same position as before the photographing was stopped when the lens barrel has to be inserted again, there is a possibility of a captured image taken before the photographing was stopped being significantly changed from one taken after photographing is resumed. In this case, the operator 3501 has to resume the surgical operation viewing a captured image photographed in a different photographing direction and photographing range from before the stop, and thus there are concerns of a burden on the operator 3501 increasing and a risk of the surgical operation escalating.

Therefore, as a countermeasure against mist and/or body fluid, a method of photographing an observation target site from a farther position in advance to prevent contamination of the objective lens of the lens barrel 3101 is also considered. However, if photographing is performed at a remote distance, it is difficult to finely photograph an observation target site, and thus it is difficult to observe a small part when treatment is being performed. Even if a treatment site is enlarged and displayed using the electronic zoom function, image quality deteriorates more than when it is photographed at a short distance, and thus it is hard to say that such photographing is optimum.

In addition, as another countermeasure against mist and/or body fluid, a method in which the operator 3501 and the endoscopist cooperate to retract the lens barrel 3101 in advance when there is mist and/or scattering of body fluid is also considered. According to this method, it is possible to continue photographing the state of the body cavity even during retraction, and thus there is a possibility of the surgical operation proceeding more safely than in the method of taking out the lens barrel 3101 for a while as described above. In this method, however, the work of bringing the lens barrel 3101 close to the observation target site again is also necessary when photographing is resumed, as in the case in which the lens barrel 3101 is taken out for a while, and thus it is difficult to reproduce the same observation state as before photographing was stopped, and thus captured images are changed. In addition, there are cases in which, when photographing continues during retraction, focus has to be re-adjusted so that a proper captured image is obtained at a position after retraction, and focus has to be adjusted again when photographing is resumed. Thus, such work results in an increasing burden on the endoscopist and an increased operation time.

To solve all the problems described above, under the retraction condition in the first embodiment that generation of mist and/or occurrence of scattering of body fluid is detected, the support arm device 3300 causes the lens barrel 3101 to automatically retract to a position at which the mist and/or body fluid does not affect the captured images. Thus, it is possible to avoid contamination of the lens barrel 3101 by the mist and/or body fluid, and states of the inside of the body cavity can be observed constantly, without the work of taking out the lens barrel 3101 for a while as in the above-described method of the related art. Therefore, a safer surgical operation can be provided. Note that, if the lens barrel 3101 automatically retracts, there is concern of the user (in particular, the endoscopist) experiencing the inconvenience of not knowing the position of the lens barrel 3101. In the first embodiment, however, when disappearance of the mist and/or settled scattering of body fluid is detected after the retraction operation, the support arm device 3300 causes the lens barrel 3101 to automatically return to its original position. Therefore, occurrence of such inconvenience can also be resolved.

In addition, since the focus control process by the focus control unit 123 and the above-described image processing by the image processing unit 122 are performed at the time of the retraction operation and return operation of the lens barrel 3101 according to the first embodiment, the display device 3403 projects substantially constant display images. That is to say, a change resulting from movement of the lens barrel 3101 seldom occurs in display provided to the operator 3501. As described above, according to the first embodiment, while stable display is maintained, contamination of the lens barrel 3101 by mist and/or body fluid can be prevented. Therefore, it is possible to smoothly execute a surgical operation, and thus shortening of an operation time, reduction of a burden on the medical staff, and reduction of a burden on the patient 3505 (reduction of invasiveness) can be realized.

1-3. Image Processing Method

A process procedure of an image processing method executed in the image processing system 1 according to the first embodiment will be described with reference to FIG. 5. FIG. 5 is a flowchart showing an example of the process procedure of the image processing method according to the first embodiment.

Note that processes of the respective steps shown in FIG. 5 correspond to processes executed by the CCU 3401 shown in FIG. 2. Specifically, the processes of Step S101 to Step S107 and the processes of Step S111 to Step S117 correspond to processes executed by the movement control unit 121 of the CCU 3401. In addition, the processes of Step S109 and Step S119 correspond to processes executed by the image processing unit 122 and the focus control unit 123 of the CCU 3401. Since details of the processes have already been described with reference to FIG. 2, detailed description of the processes will be omitted in the following description of the process procedure of the image processing method.

In addition, during the series of processes shown in FIG. 5, the image sensor 111 of the endoscope 3100 acquires an image signal when necessary, and the image processing unit 122 of the CCU 3401 generates image data related to a captured image and image data related to a display image based on the image signal. Then, the display image is displayed on the display device 3403 based on the generated image data related to the display image.

Referring to FIG. 5, first in the image processing method according to the first embodiment, whether generation of mist has been detected is determined (Step S101). Specifically, whether generation of mist has been detected is determined based on the image data related to the captured image in Step S101.

When generation of mist has not been detected in Step S101, no retraction operation of the lens barrel 3101 is performed, and thus the image processing method ends. On the other hand, when generation of mist has been detected in Step S101, the process proceeds to Step S103.

In Step S103, a retraction movement amount of the lens barrel 3101 is decided. In the first embodiment, a predetermined value set in advance by the user is used as the retraction movement amount.

Next, whether a current position of the lens barrel 3101 is a final position, i.e., whether it has moved the retraction movement amount decided in Step S103, is determined (Step S105). When it is immediately after generation of mist is detected but before a retraction operation is started, the current position of the lens barrel 3101 is of course not the final position. In this case, the process proceeds to Step S107.

In Step S107, an instruction to move the lens barrel 3101 in the retraction direction is issued. According to this instruction, the actuator driving control unit 131 of the arm control device 3407 shown in FIG. 2 drives the actuators 141 provided in the respective joints of the arm unit 3303 of the support arm device 3300, and thereby the lens barrel 3101 is moved in the retraction direction.

Next, while the lens barrel 3101 is moving in the retraction direction, focus is controlled to be on the observation target site, a captured image is cut out, and then an electronic zoom process is performed such that the display range of the display image becomes the same as before the retraction operation (Step S109). That is, image data related to the display image is generated such that the display range of the display image becomes the same as before the retraction operation.

When the process of Step S109 ends, the process returns to Step S105, and the process of determining whether the current position of the lens barrel 3101 is the final position is performed again. Thereafter, the processes of Step S105 to Step S109 are repeated until the current position of the lens barrel 3101 is determined to be the final position in Step S105, i.e., until the lens barrel 3101 is moved the retraction movement amount. Accordingly, substantially the same display image is displayed during the retraction operation.

When the current position of the lens barrel 3101 is determined to be the final position in Step S105, the process proceeds to Step S111. In Step S111, it is determined whether disappearance of the mist has been detected. Specifically, it is determined in Step S111 whether disappearance of the mist has been detected based on the image data related to the captured image.

When disappearance of the mist has not been detected in Step S111, the lens barrel stands by as it is, and for example, after a predetermined period of time corresponding to the frame rate of the captured image, the determination process of Step S111 is repeated. That is, the lens barrel 3101 stands by at the retracted position until the mist disappears.

When disappearance of the mist has been detected in Step S111, the process proceeds to Step S113. In Step S113, a return movement amount of the lens barrel 3101 is decided. In the first embodiment, the same value as the retraction movement amount is used as the return movement amount.

Next, it is determined whether the current position of the lens barrel 3101 is a final position, i.e., whether the lens barrel has been moved the return movement amount decided in Step S113 (Step S115). The current position of the lens barrel 3101 is of course not the final position immediately after disappearance of the mist is detected and before the return operation is started. In this case, the process proceeds to Step S117.

In Step S117, an instruction to move the lens barrel 3101 in the return direction is issued. According to this instruction, the actuator driving control unit 131 of the arm control device 3407 shown in FIG. 2 drives the actuators 141 provided in the respective joints of the arm unit 3303 of the support arm device 3300, and thereby the lens barrel 3101 is moved in the return direction.

Next, while the lens barrel 3101 is moving in the return direction, focus is controlled to be on the observation target site, a captured image is cut out, and then an electronic zoom process is performed so that the display range of a display image becomes the same as before the retraction operation (Step S119). That is, image data related to the display image is generated such that the display range of the display image becomes the same as before the retraction operation.

When the process of Step S119 ends, the process returns to Step S115, and the process of determining whether the current position of the lens barrel 3101 is the final position is performed again. Thereafter, the processes of Step S115 to Step S119 are repeated until the current position of the lens barrel 3101 is determined to be the final position in Step S115, i.e., the lens barrel 3101 moves the return movement amount. Accordingly, substantially the same display image is displayed even during the return operation.

When the current position of the lens barrel 3101 is determined to be the final position in Step S115, the series of processes of the image processing method ends. In the first embodiment, the above-described series of processes is executed when necessary while the endoscope 3100 is photographing the observation target site during the surgical operation.

The process procedure of the image processing method according to the first embodiment has been described above.

2. Second Embodiment

A second embodiment of the present disclosure will be described with reference to FIG. 6. FIG. 6 is a block diagram showing an example of a configuration of an image processing system according to the second embodiment. Note that, since an endoscopic surgery system to which the image processing system according to the second embodiment can be applied is similar to the endoscopic surgery system 3000 shown in FIG. 1, description thereof will be omitted here.

Referring to FIG. 6, the image processing system 2 according to the second embodiment corresponds to a system with changed functions of the endoscope 3100 and CCU 3401 from the image processing system 1 according to the first embodiment shown in FIG. 2. Since other configurations of the image processing system 2 are similar to the image processing system 1, description of subjects overlapping with the image processing system 1 will be omitted there. In addition, an image processing method according to the second embodiment is similar to the image processing method according to the first embodiment except that a method of deciding a retraction movement amount to be described below is different and a process of determining execution of a retraction operation based on the retraction movement amount is added, and thus description thereof will be omitted.

An image sensor 111 and a focus adjustment mechanism 112 are mounted in an endoscope 3100a according to the second embodiment. The elements are similar to those mounted in the endoscope 3100 of the image processing system 1 according to the first embodiment. In the second embodiment, the endoscope 3100a has a distance detection unit 113 as a function, unlike in the first embodiment.

The distance detection unit 113 detects a distance from the leading end of a lens barrel 3101 of the endoscope 3100a to an observation target site in the optical axis direction of an objective lens of the lens barrel 3101 (i.e., a distance in the stretching direction of the lens barrel 3101). The distance detection unit 113 transmits detected distance information to a CCU 3401a.

Note that there is no specific limit on the configuration of the distance detection unit 113. For example, when a stereo camera is mounted in the endoscope 3100a, the distance detection unit 113 can be the stereo camera. Since a captured image obtained from the stereo camera includes depth information of an object present in the captured image, the distance can be detected from the captured image of the stereo camera. Note that, although the distance detection unit 113 is illustrated as a function of the endoscope 3100a in FIG. 2 for the sake of convenience, strictly speaking, when the distance is detected from the captured image of the stereo camera, a processor included in the CCU 3401a calculates the distance based on an image signal acquired by the stereo camera. For this reason, it can be said that the function of the distance detection unit 113 is realized by the stereo camera of the endoscope 3100a and the processor of the CCU 3401a.

Alternatively, for example, the distance detection unit 113 can be a distance measurement sensor provided at the leading end of the lens barrel 3101. If the distance measurement sensor is provided, however, there are concerns of the lens barrel 3101 having a larger size and invasiveness growing accordingly. In addition, there is concern that costs incurred due to the provided distance measurement sensor will increase. Thus, it is desirable to realize the distance detection unit 113 with a stereo camera.

In the second embodiment, the CCU 3401a has a movement control unit 121a, an image processing unit 122, and a focus control unit 123 as functions. Functions of the image processing unit 122 and the focus control unit 123 are similar to those of the first embodiment. In the second embodiment, a function of the movement control unit 121a is different from that in the first embodiment.

Specifically, when a distance between the leading end of the lens barrel 3101 and the observation target site at which the mist does not affect the captured image is set to X1 and a distance between the leading end of the lens barrel 3101 and the observation target site immediately before generation of mist is detected is set to X2, the movement control unit 121a decides a retraction movement amount X3 through X3=X1−X2. The distance X2 is one detected by the above-described distance detection unit 113 immediately before generation of mist is detected. In addition, the distance X1 may be appropriately decided by the user based on past experience. For example, when an amount of generated mist has a tendency according to a type of biological tissue that is the observation target site, a type of the energy device 3203, an operation method, or the like, the distance X1 may be decided based on the tendency obtained from past knowledge.

In addition, when the retraction movement amount X3>0, the movement control unit 121a issues an instruction to the arm control device 3407 to cause a retraction operation to be performed by the retraction movement amount X3. In the retraction operation, the arm control device 3407 causes the lens barrel 3101 to move the retraction movement amount X3. In this case, since X3=X1−X2 as described above, the lens barrel 3101 is moved so that its leading end is placed at a position the distance X1 away from the observation target site at which mist does not affect the captured image.

On the other hand, when the retraction movement amount X3<0, the movement control unit 121a does not issue an instruction to perform a retraction operation. This is because, when the retraction movement amount X3<0, even if generation of mist has been detected, the lens barrel 3101 is already at a distance at which the mist does not affect the captured image, and thus there is no necessity to perform a retraction operation.

Note that, since other functions of the movement control unit 121a are similar to those of the movement control unit 121 according to the first embodiment, description thereof will be omitted.

The second embodiment has been described above. According to the second embodiment, the distance X2 between the leading end of the lens barrel 3101 and the observation target site immediately before generation of mist is detected is detected, and based on the distance X2 and the distance X1 between the leading end of the lens barrel 3101 and the observation target site at which the mist does not affect the captured image, the retraction movement amount X3 is decided using X3=X1−X2 as described above. In addition, the retraction operation is executed only when the retraction movement amount X3>0.

Here, the retraction movement amount of the first embodiment is a given value set in advance. Thus, if the lens barrel 3101 is retracted based on the retraction movement amount, there are possibilities of the lens barrel 3101 being retracted farther than necessary and the retraction operation being executed even though the lens barrel 3101 is already sufficiently away from the observation target site and thus there is no necessity for it to be retracted.

On the other hand, in the second embodiment, the lens barrel 3101 is retracted a minimum necessary amount at which mist does not affect the captured image taking the distances X1 and X2 into account as described above. In addition, when the lens barrel 3101 is already sufficiently away from the observation target site, no retraction operation is performed. For example, as a retraction movement amount becomes greater, the magnification of electronic zoom with respect to a display image increases accordingly, and thus there is concern of image quality becoming poor. In the second embodiment, however, the retraction operation of the lens barrel 3101 is minimized, i.e., it is possible to perform no retraction if there is no necessity for it as described above, and thus the operator can be provided with the image more stably.

3. Third Embodiment

A process procedure of an image processing method according to a third embodiment of the present disclosure will be described with reference to FIG. 7. FIG. 7 is a flowchart showing an example of the process procedure of the image processing method executed in an image processing system according to the third embodiment. Note that, since an endoscopic surgery system to which the image processing system according to the third embodiment can be applied is similar to the endoscopic surgery system 3000 shown in FIG. 1, description thereof will be omitted here. The image processing system according to the third embodiment corresponds to a configuration in which the function of a movement control unit 121 of a CCU 3401 is changed from the image processing system 1 according to the first embodiment shown in FIG. 2, and thus description of the image processing system according to the third embodiment will be omitted here. While the process procedure of the image processing method will be described with reference to FIG. 7, the function of the movement control unit according to the third embodiment will also be described here.

Note that processes of Step S201 to Step S205, Step S209 to Step S211, and Step S215 of the processes shown in FIG. 7 correspond to processes executed by the movement control unit of the CCU 3401. In addition, the processes of Step S207 and Step S213 correspond to processes executed by an image processing unit 122 and a focus control unit 123 of the CCU 3401. Detailed description of processes among the processes shown in FIG. 7 similar to those of the first embodiment will be omitted.

In addition, in the third embodiment, an image sensor 111 of an endoscope 3100 acquires an image signal during the series of processes shown in FIG. 7 when necessary, and the image processing unit 122 of the CCU 3401 generates image data related to a captured image and image data related to a display image based on the image signal as in the first embodiment. In addition, the display image is displayed on the display device 3403 based on the generated image data related to the display image.

Referring to FIG. 7, in the image processing method according to the third embodiment, whether generation of mist has been detected is determined first (Step S201). The process of Step S201 is similar to the process of Step S101 shown in FIG. 5 of the first embodiment.

When no generation of mist has been detected in Step S201, no retraction operation of the lens barrel 3101 is performed, and thus the image processing method ends. On the other hand, when generation of mist has been detected in Step S201, the process proceeds to Step S203.

In Step S203, it is determined whether mist presence areas occupy 30% or more of the captured image. Specifically, in Step S203, the captured image is divided into a number of areas based on the image data related to the captured image, and it is determined whether mist is present in each of the areas through an image recognition process. Then, based on the result, a ratio of mist presence areas occupying the captured image is calculated, and the value is compared to the threshold value of 30%. Note that a method of calculating a ratio of mist presence areas occupying the captured image is not limited thereto, and any of various methods may be used.

When the mist presence areas are determined to occupy 30% or more of the captured image in Step S203, an instruction to move the lens barrel 3101 in the retraction direction is issued (Step S205), and according to the instruction, the arm control device 3407 controls driving of the arm unit 3303 of the support arm device 3300 to move the lens barrel 3101 in the retraction direction. Then, while this lens barrel 3101 is being moved in the retraction direction, focus is controlled to be on the observation target, and cutting-out of the captured image and an electronic zoom process are performed so that a display range of the display image is the same as before the retraction operation (Step S207). The processes of Step S205 and Step S207 are similar to the processes of Step S107 and Step S109 shown in FIG. 5 in the first embodiment.

When the process of Step S207 ends, the process returns to Step S203, and the process of determining whether the mist presence areas occupy 30% or more of the captured image is performed again. Thereafter, the processes of Step S203 to Step S207 are repeated until the mist presence areas are determined to occupy less than 30% of the captured image in Step S203. Accordingly, substantially the same display image is displayed during the retraction operation.

As described above, in the third embodiment, the movement control unit issues an instruction to perform a retraction operation under the retraction condition that mist presence areas occupy a first predetermined ratio of the captured image, unlike in the first embodiment. In addition, in that case, the retraction operation continues until the mist presence areas occupy less than 30% of the captured image, with no retraction movement amount decided and instruction to perform a retraction operation issued. Since the growing number of mist presence areas occupying the captured image means that a distance between the leading end of the lens barrel 3101 and a mist generation position is short, by performing a retraction operation when mist presence areas occupy a higher ratio than the predetermined ratio of the captured image as described above, the lens barrel 3101 can be retracted to be farther away from the mist generation position.

When the mist presence areas are determined to occupy less than 30% of the captured image in Step S203, the process proceeds to Step S209. In Step S209, it is determined whether the mist presence areas occupy 25% or less of the captured image. Specifically, in Step S209, the ratio of the mist presence areas occupying the captured image are calculated in a method similar to that of Step S203 described above, and the value is compared to the threshold value of 25%.

When it is determined that the mist presence areas occupy more than 25% of the captured image in Step S209, the process returns to Step S203, and a process of determining whether the mist presence areas occupy 30% or more of the captured image is performed again. Then, the process proceeds to any of Step S205 and Step S209 again according to the result.

On the other hand, when it is determined that the mist presence areas occupy 25% or less of the captured image in Step S209, an instruction to move the lens barrel 3101 in the return direction is issued (Step S211), and the arm control device 3407 controls driving of the arm unit 3303 of the support arm device 3300 to move the lens barrel 3101 in the return direction according to the instruction. Then, while this lens barrel 3101 is being moved in the return direction, focus is controlled to be on the observation target, and cutting-out of the captured image and an electronic zoom process are performed so that a display range of the display image is the same as before the retraction operation (Step S213). The processes of Step S211 and Step S213 are similar to those of Step S117 and Step S119 shown in FIG. 5 in the first embodiment.

As described above, in the third embodiment, the movement control unit issues an instruction to perform a return operation under the return condition that the mist presence areas occupy a second predetermined ratio or less of a captured image, unlike in the first embodiment. When the mist presence areas occupy the predetermined ratio or less of the captured image, the lens barrel 3101 is sufficiently away from a mist generation position or mist has settled down from the generation. Thus, if a return operation is performed based on such a return condition, movement of the lens barrel 3101 can be controlled so that the lens barrel 3101 is not moved farther away from the mist generation position than necessary.

When the process of Step S213 ends, it is determined whether the return operation has ended (Step S215). Specifically, whether the return operation has ended is determined based on whether the lens barrel 3101 has returned to the original position before the retraction operation is performed. Alternatively, whether the return operation has ended may be determined by separately setting a return movement amount and determining whether the lens barrel 3101 has returned the return movement amount in the return direction from the position at which the lens barrel is retracted most.

When the return operation is determined not to have ended in Step S215, the process returns to Step S203, and a process of determining whether the mist presence areas occupy 30% or more of the captured image is performed. Then, according to the result, the process proceeds to any of Step S205 and Step S209 again. In this manner, the processes of determining the mist presence areas occupying the captured image are repeatedly executed in Step S203 and Step S209 until the series of processes of the image processing method ends in the third embodiment. Then, the lens barrel 3101 performs the retraction operation if the mist presence areas occupy the first predetermined ratio or more of the captured image, and the lens barrel 3101 performs the return operation if the mist presence areas occupy the second predetermined ratio or less of the captured image. Thus, when generation of mist has been detected, the lens barrel 3101 can be moved so that the lens barrel 3101 is moved a first predetermined distance or farther from the mist generation position in which the mist presence areas occupy less than the first predetermined ratio, and is not excessively moved a second predetermined distance, which is different from the first distance, or farther therefrom.

When the return operation is determined to have ended in Step S215, even if the lens barrel 3101 is brought close to the mist generation position, the mist presence areas occupy 25% or less of the captured image. In other words, the generation of mist has settled down to the extent that it does not affect the captured image, and thus the series of processes of the image processing method ends in that case. In the third embodiment, the series of processes described above are executed when necessary while the endoscope 3100 is photographing the observation target site during the surgical operation.

The process procedure of the image processing method according to the third embodiment has been described above. Note that, although the first ratio of the mist presence areas occupying a captured image, which is a criterion for determining whether a retraction operation should be performed, is set to 30% and the second ratio of the mist presence areas occupying the captured image, which is a criterion for determining whether a return operation should be performed, is set to 25% in the above-described example, these values are merely examples. In the third embodiment, these first and second threshold values may be appropriately set by a user based on past experience or the like. The first and second ratios may be appropriately set to values at which vivid captured images can be obtained without the objective lens of the lens barrel 3101 being contaminated by mist based on, for example, a relation between mist presence areas occupying a captured image and influence of the mist on the captured image obtained from past knowledge.

Here, the lens barrel 3101 is retracted in order to avoid contamination of the objective lens of the lens barrel 3101 mainly by mist in the above-described first and second embodiments. After mist is generated, however, even if the objective lens would not be contaminated directly by the mist, the mist fills the photographing range, which blocks visibility, and thus difficulty in obtaining vivid captured images is a concern. To this end, according to the third embodiment, the lens barrel 3101 is retracted according to a ratio of mist presence areas occupying the captured image as described above. Even if a mist generation amount is assumed to be the same, a ratio of mist presence areas occupying a captured image decreases as the lens barrel 3101 is retracted, and thus a more vivid captured image can be obtained. As described above, according to the third embodiment, not only can contamination of the objective lens of the lens barrel 3101 by mist be avoided, but also proper images can be provided more stably even when photographing can be difficult due to mist filling the photographing range.

4. Modified Examples

Several modified examples of the above-described first to third embodiments will be described.

4-1. Other Method for Detection of Mist Based on Captured Image

In the examples of the configurations described above, when generation of mist is detected from image data related to a captured image, the movement control units 121 and 121*a* of the CCUs 3401 and 3401*a* target a whole captured image to detect generation of mist from the image data related to the captured image. However, the first and second embodiments are not limited thereto. The movement control units 121 and 121*a* may set a mist detection target area in a part inside a captured image, and perform a process of detecting generation of mist only on the mist detection target area.

A modified example in which such a mist detection target area is set in a part inside a captured image will be described as a modified example of the first and second embodiments with reference to FIGS. 8A and 8B. FIGS. 8A and 8B are diagrams for describing a method of detecting generation of mist according to the modified example in which a mist detection target area is set in a part inside a captured image. Note that the present modified example is different from the first and second embodiments in terms of details of the mist detection process, and other subjects are similar to the first and second embodiments. Thus, only differences of the present modified example from the first and second embodiments will be described below.

FIGS. 8A and 8B schematically show an example of a captured image 217 obtained from the endoscope 3100 during a surgical operation. As illustrated, the captured image 217 includes an energy device 3203, and a treatment site 219 on which treatment is performed with the energy device 3203.

In the modified example, when mist is detected, a movement control unit first detects a leading end 221 of the energy device 3203 from the captured image as shown in FIG. 8A. In the process of detecting the leading end 221 of this energy device 3203, any of various known image recognition technologies may be used. Note that the leading end 221 is formed as a grip mechanism in the illustrated example, and in a state in which the treatment site is caught by the grip mechanism, the energy device 3203 cauterizes and excises the treatment site by applying a high-frequency current to the grip mechanism.

The movement control unit sets a mist detection target area 223 as an area near the detected leading end 221 of the energy device 3203. This is because mist is generated in the vicinity of the leading end 221 practically performing treatment on the treatment site.

In this state, the movement control unit performs a mist detection process for the set mist detection target area 223. FIG. 8B schematically shows a state in which mist 201 is generated in the mist detection target area 223.

In the present embodiment, a mist detection process is not performed on a whole captured image, but a mist detection target area is set in a part inside a captured image and a mist generation detection process is performed only on the mist detection target area as described above. By limiting a target to a partial area in this manner, a load imposed on a processor included in the movement control unit in the mist detection process can be reduced.

Note that, although detection of generation of mist is set as a retraction condition in the above description, when scattering of body fluid such as blood is set as a retraction condition instead of or along with generation of mist, the configuration of the present modified example may be applied to detection of scattering of body fluid such as blood. Specifically, the movement control unit detects a leading end of a treatment instrument that may cause scattering of body fluid from a captured mage, and sets a body fluid scattering detection target area in the vicinity of the leading end. Then, the movement control unit performs a process of detecting scattering of body fluid only in the body fluid scattering detection target area. Accordingly, like when generation of mist is detected, a load imposed on the processor resulting from the body fluid scattering detection process can be reduced.

4-2. Other Examples of Retraction Condition and Return Condition

In above description, the retraction condition and the return condition of the lens barrel 3101 are set respectively to detection of generation of mist and detection of disappearance of mist in the first and second embodiments. However, the first and second embodiments are not limited thereto. In the first and second embodiments, the movement control units 121 and 121a of the CCUs 3401 and 3401a may issue respective instructions that a retraction operation and a return operation be performed under another retraction condition and return condition.

Here, several modified examples with different retraction conditions and return conditions of the lens barrel 3101 will be described. Note that respective modified examples with regard to the retraction conditions and return conditions to be described below are merely different from the first and second embodiments in terms of the retraction conditions and return conditions, and other subjects thereof are similar to those of the first and second embodiments. Thus, only differences of the modified examples from the first and second embodiments will be mainly described below.

4-2-1. Distance Between Treatment Instrument and Treatment Site

In the first and second embodiments, distances between a treatment instrument and a treatment site may be a retraction condition and a return condition. FIGS. 9A and 9B are diagrams for describing a modified example in which distances between a treatment instrument and a treatment site are a retraction condition and a return condition. FIGS. 9A and 9B schematically show a state of the inside of a body cavity of a patient undergoing an endoscopic surgical operation.

In the present modified example, a movement control unit detects a treatment instrument that can cause mist and a leading end thereof from a captured image based on image data related to the captured image to determine whether a retraction condition or a return condition is satisfied. In the example shown in FIG. 9A, the energy device 3203 and the leading end 221 thereof are shown as detection targets. Note that any of various known image recognition technologies may be used in a detection process of the energy device 3203 and the leading end 221 thereof.

Then, the movement control unit calculates a distance d between the leading end 221 of the energy device 3203 and the treatment site positioned in the direction in which the leading end 221 of the energy device 3203 faces. More specifically, the movement control unit assumes the intersection of an extended line in the direction of the leading end 221 of the energy device 3203 and a surface of an organ 224 that includes the treatment site as a point of interest Q of the energy device 3203 as shown in FIG. 10, and calculates the distance between the leading end 221 of the energy device 3203 and the point of interest Q as the distance between the leading end 221 of the energy device 3203 and the treatment site. FIG. 10 is a diagram for describing the point of interest Q of the energy device 3203.

The point of interest Q can be calculated based on 3-dimensional position information of the energy device 3203 and the organ 224. The 3-dimensional position information can be obtained from the captured image when the endoscopes 3100 and 3100a are stereo cameras. Alternatively, by separately inserting a plurality of distance measurement sensors into the body cavity of the patient, the 3-dimensional position information may be obtained based on detection values of the distance measurement sensors.

Based on the 3-dimensional information obtained as above, for example, the movement control unit can obtain spatial coordinates of the point of interest Q of the energy device 3203 using, for example, methods of JP 2015-228954A and JP 2015-228955A which are prior applications of the applicant of the present application. Then, the movement control unit calculates the distance d between the point of interest Q and the leading end 221 from the spatial coordinates of the point of interest and spatial coordinates of the leading end 221 obtained from the 3-dimensional information of the energy device 3203.

The movement control unit determines whether a retraction operation should be performed and whether a return operation should be performed based on the distance d between the leading end 221 of the energy device 3203 and the treatment site. For example, the movement control unit issues an instruction to cause the lens barrel 3101 to perform a retraction operation under the retraction condition that the distance d is equal to or shorter than a first predetermined threshold value. In addition, for example, the movement control unit issues an instruction to cause the lens barrel 3101 to perform a return operation under the return condition that the distance d is equal to or longer than a second predetermined threshold value as a result of the performed retraction operation. When mist has been generated as a result of treatment performed by the energy device 3203, the first and second threshold values can be appropriately set as values at which the mist is not likely to affect the captured image.

Note that the first threshold value for the retraction condition and the second threshold value for the return condition may be the same values or different values. For example, thus when the second threshold value is set to be greater than the first threshold value, the return operation may not be performed after the lens barrel 3101 is retracted unless the energy device 3203 is moved sufficiently away from the treatment site, and it is possible to properly limit excessive movement of the lens barrel 3101.

Note that, although distances between the treatment instrument that can cause mist and the treatment site are used as the retraction condition and the return condition in the above description, distances between a treatment instrument and a treatment site may be used as a retraction condition and a return condition with the treatment instrument that can cause scattering of body fluid such as blood, rather than the treatment instrument that can cause mist. In addition, although the distances between the treatment instrument and the treatment site are calculated based on the 3-dimensional information of the biological tissue including the treatment instrument and the treatment site in the above-described example, the distances may be obtained using another method by providing, for example, a distance measurement sensor at the leading end of the treatment instrument.

According to the present modified example described above, the instruction to perform the retraction operation is issued to the lens barrel 3101 under the retraction condition that the treatment instrument that can cause mist or scattering of body fluid and the treatment site are within a predetermined distance. Thus, the retraction operation can be performed before mist or scattering of body fluid is actually caused, and thus it is possible to reliably avoid contamination of the lens barrel 3101.

4-2-2. State of Energy Device

In the first and second embodiments, states of the energy device 3203 may be used as a retraction condition and a return condition. FIG. 11 is a block diagram showing a configuration of an image processing system according to a modified example in which states of the energy device 3203 are used as a retraction condition and a return condition. Note that an image processing system 1a according to the present modified example corresponds to a configuration in which the treatment instrument control device 3411 shown in FIG. 1 is added to the image processing system 1 according to the first embodiment shown in FIG. 2 as its constituent element and a part of the function of the movement control unit 121 is changed due to the different retraction condition and return condition. Other configurations of the image processing system 1a are similar to those of the image processing system 1, and thus overlapping description with the image processing system 1 will be omitted here.

As illustrated, in the image processing system 1a according to the present modified example, information regarding a state of a treatment instrument is transmitted from the treatment instrument control device 3411 to a CCU 3401b when necessary. In the present modified example, a movement control unit 121b determines whether the retraction condition or the return condition is satisfied based on the information regarding the state of the treatment instrument.

Specifically, the information regarding the state of the treatment instrument includes information regarding whether the energy device 3203 has been activated. The movement control unit 121b issues an instruction to cause the lens barrel 3101 to perform the retraction operation under the retraction condition that the energy device 3203 is activated (i.e., the energy device 3203 is energized) based on the information regarding the state of the treatment instrument. In addition, based on the information regarding the state of the treatment instrument, the movement control unit 121b issues an instruction to cause the lens barrel 3101 to perform the return operation under the return condition that output of the energy device 3203 stops (i.e., the energy device 3203 stops being energized) and disappearance of mist is detected based on a captured image.

Alternatively, the information regarding the state of the treatment instrument includes information regarding manipulation of a handle performed by an operator 3501 to open or close a grip mechanism at the leading end of the energy device 3203. FIG. 12 is a diagram showing a state in which the operator 3501 is using the energy device 3203. As illustrated, the handle 225 is provided on the base end side of the energy device 3203, and as the operator 3501 manipulates the handle 225, the grip mechanism at the leading end 221 is opened or closed. That is, a state in which the operator 3501 is manipulating the handle 225 to close the grip mechanism of the energy device 3203 means that treatment with the energy device 3203 is being performed. In addition, a state in which the operator 3501 is manipulating the handle 225 to open the grip mechanism of the energy device 3203 means that treatment with the energy device 3203 has ended.

The movement control unit 121b issues an instruction to cause the lens barrel 3101 to perform the retraction operation under the retraction condition that the operator 3501 manipulates the handle 225 to close the grip mechanism of the energy device 3203 based on the information regarding the state of the treatment instrument. In addition, based on the information regarding the state of the treatment instrument, the movement control unit 121b issues an instruction to cause the lens barrel 3101 to perform the return operation under the return condition that the operator 3501 manipulates the handle 225 to open the grip mechanism of the energy device 3203 and disappearance of mist is detected based on a captured image.

That the energy device 3203 is activated and that the operator manipulates the handle 225 to close the grip mechanism of the energy device 3203 respectively mean that treatment will be performed soon using the energy device 3203 and treatment is being performed using the energy device 3203, and thus these actions of the operation can be said to be actions that are highly likely to generate mist. Thus, in the present modified example, by setting one of these actions as a retraction condition, the retraction operation can be performed before mist is actually generated, and thus it is possible to reliably avoid contamination of the lens barrel 3101.

4-2-3. Detection of Movement of Leading End of Energy Device

In the first and second embodiments, movements of the leading end of the energy device 3203 may be used as a retraction condition and a return condition. In the present modified example, a movement control unit detects the leading end of the energy device from a captured image, and a movement thereof, i.e., an opening or closing operation of the grip mechanism (the grip mechanism provided at the leading end 221 shown in FIG. 12). Note that any of various known image recognition technologies may be used for detection of the leading end of the energy device and detection of movement thereof.

In addition, the movement control unit issues an instruction to cause the lens barrel 3101 to perform a retraction operation under the retraction condition that an operation of the grip mechanism at the leading end of the energy device 3203 to grip a part of biological tissue that corresponds to a treatment site is detected. In addition, the movement control unit issues an instruction to cause the lens barrel 3101 to perform a return operation under the return condition that an operation of the grip mechanism at the leading end of the energy device 3203 to release the part of the biological tissue that corresponds to the treatment site is detected and disappearance of mist is detected based on a captured image.

Note that, although, with respect to a treatment instrument that can cause mist, operations of the grip mechanism at the leading end of the energy device 3203 are used as the retraction condition and the return condition in above description, with respect to a treatment instrument that can cause body fluid such as blood to scatter, operations of the leading end of the treatment instrument (for example, a forceps, etc.) may be used as a retraction condition and a return condition. In this case, for example, the movement control unit issues an instruction to cause the lens barrel 3101 to perform a retraction operation under the retraction condition that the leading end of the treatment instrument performs treatment on a treatment site, i.e., an operation that can cause body fluid to scatter is detected based on a captured image. In addition, for example, the movement control unit issues an instruction to cause the lens barrel 3101 to perform a return operation under the return condition that the leading end of the treatment instrument does not perform treatment on the treatment site, i.e., no manipulation that can cause body fluid to scatter is detected based on a captured image, and scattering of body fluid such as blood is detected to have settled down based on a captured image.

As described in the present modified example, by performing the retraction operation according to movement of the leading end of the treatment instrument such as the energy device 3203, the retraction operation can be performed before mist and/or scattering of body fluid such as blood are actually caused, and thus it is possible to reliably avoid contamination of the lens barrel 3101.

4-2-4. Instruction from User

In the first and second embodiments, instructions of a user (for example, the operator 3501 or an endoscopist) may be used as a retraction condition and a return condition. FIG. 13 is a block diagram showing a configuration of an image processing system according to a modified example in which instructions of a user are used as a retraction condition and a return condition. Note that an image processing system 1*b* according to the present modified example corresponds to a configuration in which the input device 3409 shown in FIG. 1 is added to the image processing system 1 according to the first embodiment shown in FIG. 2 and a part of the functions of the movement control unit 121 is changed due to the different retraction condition and return condition. Other configurations of the image processing system 1*b* are similar to those of the image processing system 1, and thus overlapping description with the image processing system 1 will be omitted here.

As illustrated, in the image processing system 1*b* according to the present modified example, a CCU 3401*c* receives input of an instruction from the user that the lens barrel 3101 be caused to perform a retraction operation and an instruction to cause the lens barrel 3101 to perform a return operation via the input device 3409. The input of instructions from the user may be performed in various forms such as a switch like the foot switch 3419 shown in FIG. 1, voice, gestures, etc. However, it can be assumed that, during a surgical operation, both hands of the operator 3501 and the endoscopist are occupied with a treatment instrument, the endoscope 3100, or the like, and thus if contactless input using voice, gestures, and the like is possible, convenience of the operator 3501 and the endoscopist can be enhanced. In the present modified example, a movement control unit 121*c* issues an instruction to cause the lens barrel 3101 to perform a retraction operation and an instruction to cause the lens barrel 3101 to perform a return operation to the arm control device 3407 using the instructions from the user as the retraction condition and return condition.

Here, in the above-described embodiments and modified examples, retraction conditions and return conditions are set for the purpose of preventing the lens barrel 3101 from being contaminated by mist and/or body fluid. However, there are cases in which the lens barrel 3101 is desired to be intentionally moved away from an observation target site for a while for other purposes, for example, securing a work space for performing treatment using a treatment instrument. In the present modified example, a retraction operation can be performed through an instruction from a user at an arbitrary timing, without changing a display image, and thus this technology is particularly effective when the lens barrel 3101 is intended to be retracted for a while.

4-2-5. Distance Between Leading End of Lens Barrel of Endoscope and Treatment Instrument In the first and second embodiments, distances between the leading end of the lens barrel 3101 of the endoscope 3100 or 3100*a* and a treatment instrument may be used as a retraction condition and a return condition. Note that the present modified example does not aim to prevent the lens barrel from being contaminated by mist and/or body fluid, unlike the above-described embodiments and modified examples. In the present modified example, by using distances between the leading end of the lens barrel 3101 of the endoscope 3100 or 3100*a* and a treatment instrument as the retraction condition and return condition, it is possible to prevent the lens barrel 3101 from being brought in unintended contact with the treatment instrument.

Specifically, in the present modified example, a distance between the leading end of the lens barrel 3101 of the endoscope 3100 or 3100*a* and the treatment instrument is detected. As a detection method of the distance, any of various methods can be used. For example, when the endoscope 3100 or 3100*a* is a stereo camera, the distance can be detected based on a captured image thereof. Alternatively, for example, by providing a distance measurement sensor at the leading end of the lens barrel 3101, the distance can be detected based on a detection value of the distance measurement sensor. Alternatively, for example, by inserting a plurality of distance measurement sensors into the body cavity of the patient, 3-dimensional position information of the lens barrel 3101 and the treatment instrument is acquired based on detection values of these distance measurement sensors, and thereby the distance can be acquired based on the 3-dimensional position information.

In the present modified example, the movement control unit determines whether a retraction operation should be performed and a return operation should be performed based on the detected distances between the leading end of the lens barrel 3101 of the endoscope 3100 or 3100*a* and the treatment instrument. For example, the movement control unit issues an instruction to cause the lens barrel 3101 to perform the retraction operation under the retraction condition that the distance is equal to or shorter than a first predetermined threshold value. In addition, for example, the movement control unit issues an instruction to cause the lens barrel 3101 to perform the return operation under the return condition that the distance resulting from the retraction operation is equal to or longer than a second predetermined threshold value. The first and second threshold values can be appropriately set as values at which contact of the lens barrel 3101 and the treatment instrument can be reliably prevented.

As described above, according to the present modified example, if the distances between the leading end of the lens barrel 3101 of the endoscope 3100 or 3100*a* and the treatment instrument are used as the retraction condition and the return condition, even when the lens barrel 3101 and the treatment instrument are likely to be brought in unintended contact with each other when they are moved inside the body cavity during a surgical operation, such contact can be prevented. In addition, while the lens barrel 3101 is moved to prevent contact, the display device maintains substantially constant display, and thus smooth continuation of the surgical operation is realized.

Note that, when a plurality of treatment instruments are inserted in the body cavity, distances between the leading end of the lens barrel 3101 of the endoscope 3100 or 3100*a* and the plurality of treatment instruments are detected, and based on these respective distances, whether a retraction operation should be performed and whether a return operation should be performed may be decided with respect to each of the treatment instruments. Thus, even when there are the plurality of treatment instruments inserted into the body cavity, contact between the lens barrel 3101 and these treatment instruments can be prevented.

In addition, in the present modified example, a return movement amount may not necessarily be the same as a retraction movement amount. In addition, the return movement amount may not be a constant value. Since the present modified example aims to prevent the lens barrel 3101 from being brought into unintended contact with a treatment instrument, it is considered more effective for fulfilling the aim that, for example, at the time of a return operation, the lens barrel 3101 returns to a position at which a distance to the treatment instrument can be more safely secured and then the lens barrel 3101 stops at that position, rather than the lens barrel 3101 returning to the original position before the retraction operation. Thus, in the present modified example, the return movement amount may be appropriately set each time a return operation is performed so that, for example, a distance between the lens barrel 3101 and the treatment instrument is maintained at a given value or longer at all times.

4-3. Other Example of Configuration of Support Arm Device

As described with reference to FIG. 1, the arm unit 3303 of the support arm device 3300 having, for example, 6 degrees of freedom supports the endoscope 31, and by controlling attitudes of the arm unit 3303, the retraction operation and return operation of the lens barrel 3101 of the endoscope 3100 are performed in the examples of the configurations described above. However, the first to third embodiments are not limited thereto. A support arm device having another configuration may move the lens barrel 3101 for the retraction operation and return operation. Note that the present modified example is similar to the first to third embodiments described above except that a configuration of the support arm device is different, and for that reason, a driving control method of the support arm device at the time of a retraction operation and a return operation is different. Thus, only differences of the present modified example from the first to third embodiments will be mainly described.

FIG. 14 is a diagram schematically showing an example of another configuration of the support arm device. Referring to FIG. 14, the support arm device 300 according to the present modified example is provided with a base unit 310 and an arm unit 230 stretching from the base unit 310. In addition, a holding unit 330 that holds the endo scope 3100 is provided at the leading end of the arm unit 320. In the present modified example, this support arm device 300 is applied to the endoscopic surgery system 3000 shown in FIG. 1, instead of the support arm device 3300 described above.

In the illustrated example, the arm unit 320 includes joint 321a, 321b, and 321d, and links 323a, 323b, and 323c, and is driven under control of the arm control device 3407 show in FIG. 1. In FIG. 14, however, the configuration of the arm unit 320 is illustrated to be simplified for the sake of simplicity. In reality, shapes, numbers, and disposition of the joints 321a to 321c and the links 323a to 323c, directions of rotation axes of the joints 321a to 321c, and the like can be appropriately set so that the arm unit 320 has a desired degree of freedom. Like the support arm device 3300 according to the first to third embodiments described above, for example, the arm unit 320 can suitably have 6 or more degrees of freedom. Accordingly, the holding unit 330 can be freely moved in a movable range of the arm unit 320, and thus the lens barrel 3101 of the endoscope 3100 can be inserted into the body cavity of the patient 3505 from a desired direction.

The holding unit 330 is a substantially cylindrical member having an inner diameter the substantially same as the outer diameter of the lens barrel 3101 of the endoscope 3100, and holds the endoscope 3100 with the lens barrel 3101 inserted into the cylinder. A slider mechanism that can move the lens barrel 3101 in its stretching direction (i.e., the optical axis direction of the objective lens) and an actuator that drives the slider mechanism are provided on the inner wall of the cylinder of the holding unit 330. As the arm control device 3407 controls driving of the actuator, the lens barrel 3101 can be moved a predetermined amount in the stretching direction. In the present modified example, the lens barrel 3101 is moved at the time of a retraction operation and a return operation using these mechanisms of the holding unit 330.

Here, since attitudes of the multi-axial arm unit 3303 of the support arm device 3300 according to the first to third embodiments described above are appropriately controlled, the lens barrel 3101 is moved at the time of a retraction operation and a return operation. In this case, in order to move the lens barrel 3101 in parallel with its stretching direction, movements of the arm unit 3303 become relatively complicated. In addition, since movements of the lens barrel 3101 should be realized by controlling rotation of the joints 3305a to 3305c of the arm unit 3303 in a coordinated manner, control becomes relatively complicated as well.

On the other hand, according to the present modified example, since the holding unit 330 having the mechanisms described above holds the lens barrel 3101 and movement in its stretching direction is realized, simpler control of the actuator of the holding unit 330 can realize the movement of the lens barrel 3101 at the time of a retraction operation and a return operation, with no necessity to drive the arm unit 320 itself.

4-4. Semi-Automatization of Retraction Operation and Return Operation

In the above examples of the configurations, the retraction operations and the return operations are, so to speak, automatically performed by the arm control device 3407 when the retraction conditions and the return conditions are satisfied. However, the first to third embodiments are not limited thereto, and when the endoscopist manipulates the endoscope 3100 in a state in which the endoscope 3100 is held by the support arm device 3300 as shown in FIG. 1, the arm control device 3407 may drive the support arm device 3300 to encourage the endoscopist to perform the retraction operation and the return operation. Note that, in the present specification, such a mode retraction operation and return operation in which driving of the support arm device 3300 is controlled to encourage the endoscopist to perform a retraction operation and a return operation will be referred to as a semi-automatic retraction operation and return operation, in order to distinguish from the so-called automatic retraction operation and return operation described so far. The present modified example is similar to the first to third embodiments described above except that the semi-automatic retraction operation and return operation are performed. Thus, differences of the present modified example from the first to third embodiments will be mainly described below.

The semi-automatic retraction operation and return operation are assumed to be performed when the endoscopist manipulates the endoscope 3100 in the state in which the endoscope 3100 is held by the support arm device 3300. In addition, driving control of the support arm device 3300 is assumed to be performed through force control. Furthermore, in this case, the endoscopist manipulates the endoscope 3100 through, for example, direct manipulation.

In the present modified example, when a retraction condition is satisfied, the arm control device 3407 drives the support arm device 3300 to give the endoscopist force in the direction in which the lens barrel 3101 is retracted (assist force in the retraction direction). Accordingly, the endoscopist recognizes that a situation in which the lens barrel 3101 should be retracted (i.e., any of the above-described retraction conditions) has been created and thus can manipulate the endoscope 3100 to perform a retraction operation according to the assist force given from the arm unit 3303.

In this case, as shown in FIG. 15 and FIG. 16, assist force Y (positively applied in the retraction direction) may change according to a distance X between the energy device 3203 and a treatment site. FIGS. 15 and 16 are diagrams for describing the assist force related to the semi-automatic retraction operation and return operation. FIG. 15 schematically shows a state of the inside of a body cavity of a patient during an endoscopic surgical operation, like FIGS. 9A and 9B. In addition, FIG. 16 schematically shows a relation between the distance X between the energy device 3203 and the treatment site and the assist force Y.

As illustrated, in the present modified example, when the distance X between the energy device 3203 and the treatment site is equal to or shorter than a predetermined threshold value thr, the assist force Y is generated in the retraction direction. In addition, the assist force Y is generated to linearly increase as the distance X between the energy device 3203 and the treatment site gets shorter. When the distance between the energy device 3203 and the treatment site is short, there is a high possibility of treatment being performed by the energy device 3203 and mist being generated accordingly. Thus, by generating the assist force Y according to the distance X as described, the endoscopist senses stronger assist force in the retraction direction when mist is highly likely to be generated, and thus the endoscopist can be informed more strongly that a situation in which the lens barrel 3101 should be retracted has been created, and the retraction operation can be smoothly performed. Note that the distance X between the energy device 3203 and the treatment site can be detected using a method similar to that described in (4-2-1. Distance between treatment instrument and treatment site) described above.

Although description with regard to the retraction operation has been provided above, the arm control device 3407 drives the support arm device 3300 at the time of a return operation to generate assist force in a return direction likewise.

Here, in the embodiments and modified examples described above, the image processing unit appropriately performs the cutting-out process and the electronic zoom process on a captured images during the period after the start of the retraction operation before the end of the return operation, and thus display of the display device 3403 is substantially constant. In general, the endoscopist recognizes a position of the lens barrel 3101 inside the body cavity and moves the lens barrel 3101 viewing the image photographed the endoscope 3100. Thus, if display on the display device 3403 is substantially constant, there is a concern of the endoscopist having difficulty manipulating the lens barrel 3101.

With regard to this, in the embodiments and modified examples other than the present modified example described above, the retraction operation and the return operation are automatically performed, so to speak, rather than being performed according to manipulation of the endoscopist. In addition, the retraction movement amount and the return movement amount are basically set to the same value, and when the return condition is satisfied after the retraction operation, the lens barrel 3101 returns to its original position. In the embodiments and modified examples, the retraction operation and the return operation are not assumed to be performed according to manipulation of the endoscopist, and even if the retraction operation and the return operation were performed, the lens barrel 3101 returns to its original position in the end. Thus, even if display of the display device 3403 is substantially constant for the period after the start of the retraction operation and before the end of the return operation, no significant problem is considered to be created.

On the other hand, in the present modified example, the retraction operation and the return operation are performed semi-automatically, i.e., the retraction operation and the return operation are performed according to manipulation of the endoscopist. Thus, if display of the display device 3403 is substantially constant during the retraction operation and the return operation, there is a concern of the endoscopist not recognizing a position of the lens barrel 3101 inside the body cavity and having difficulty performing manipulation for the retraction operation and the return operation.

Thus, in the present modified example, an indicator 229 indicating a current distance between the leading end of the lens barrel 3101 and an organ 231 that is an observation target site may be superimposed on a display image and displayed on a display screen 227 as shown in FIG. 17. Display control of the indicator 229 can be performed by the image processing unit of the CCU. FIG. 17 is a diagram showing an example of display of a distance between the leading end of the lens barrel 3101 and the observation target site on the display screen. Note that, although the indicator 229 is used in the illustrated example to indicate a distance, more specifically, the distance may be displayed using a numerical value.

The modified example in which the retraction operation and the return operation are semi-automatically performed has been described above. Here, if the above-described so-called automatic retraction operation and return operation are performed when the endoscopist directly manipulates the endoscope 3100 held by the support arm device 3300 that is driven through force control, there is a possibility of relatively strong force being suddenly exerted on the endoscopist, which causes a concern of a manipulation capability of the endoscopist deteriorating. On the other hand, in the present modified example, relatively weak assist force enough to encourage a retraction operation and a return operation is generated, and thus manipulation of the endoscopist is the only primary agent for executing the retraction operation and the return operation. Thus, when the endoscope 3100 held by the support arm device 3300 that is driven through force control is assumed to be directly manipulated by the endoscopist, such a semi-automatic retraction operation and return operation according to the present modified example are executed, and thus without deteriorating the manipulation capability of the endoscopist, the retraction operation and the return operation can be performed more smoothly.

Note that, in the present modified example, a function of notifying the endoscopist of return of the lens barrel 3101 to a return position (i.e., the original position before a retraction operation) in the return operation may be provided in the image processing system. The reason for this is that, because substantially constant display of the display device 3403 is maintained during the period from the start of the retraction operation to the end of the return operation, the endoscopist is not able to recognize that the distance between the leading end of the lens barrel 3101 and the observation target site is short when the endoscopist has moved the lens barrel 3101 near the observation target site at the time of the return operation. For example, even if the indicator 229 described above is superimposed and displayed, it is difficult to intuitively recognize the distance between the leading end of the lens barrel 3101 and the observation target site, and therefore it is preferable to further provide the notification function.

The notification may be performed using any of various methods. For example, the arm control device 3407 may generate pulsating assist force. In addition, for example, the CCU may cause the display screen to display any type of notification other than the indicator 229. In addition, for example, when the endoscopist wears an HMD or any wearable device on his or her body, the wearable device may perform the notification by any of various mechanisms including vibration, voice, display, etc.

5. Supplement

It should be understood by those skilled in the art that various modifications, combinations, sub-combinations and alterations may occur depending on design requirements and other factors insofar as they are within the scope of the appended claims or the equivalents thereof.

Further, the effects described in this specification are merely illustrative or exemplified effects, and are not limitative. That is, with or in the place of the above effects, the technology according to the present disclosure may achieve other effects that are clear to those skilled in the art based on the description of this specification.

For example, a configuration of the endoscopic surgery system to which the image processing system according to each embodiment and each modified example described above can be applied is not limited to the example shown in FIG. 1. The image processing system according to each embodiment and each modified example can be applied to various endoscopic systems. In addition, a configuration of the image processing system according to each embodiment and each modified example is not limited to the examples shown in FIGS. 2, 6, 11 and 13. The image processing system may execute the above-described processes as a whole, and a configuration thereof may be arbitrary. For example, devices constituting the image processing system, particularly the functions of the CCUs 3401, 3401*a*, 3401*b*, and 3401*c*, and the arm control device 3407 may each be realized by a single device or by a plurality of arbitrary devices in a cooperative manner.

Furthermore, a computer program for the functions of the devices constituting the image processing system according to each embodiment and each modified example described above, particularly the functions of the CCUs and the arm control device, can be produced and installed in a processing device such as a PC. In addition, a recording medium that stores such a computer program and is readable by a computer can also be provided. The recording medium is, for example, a magnetic disk, an optical disc, a magneto-optical disc, a flash memory, or the like. Further, the computer program may be distributed via, for example, a network, without using the recording medium.

In addition, the configurations that each embodiment and each modified example describe above can have can be applied in combination in a possible range. For example, some of the retraction conditions and the return conditions described in (4-2. Other examples of retraction condition and return condition) above may be combined and set. In this case, if any of the plurality of set retraction conditions and any of the plurality of set return conditions is satisfied, a retraction operation and a return operation can be respectively executed.

Additionally, the present technology may also be configured as below.

(1)

An image processing device including:
 circuitry configured to generate image data from an image captured by an endoscope of an inside of a body of a patient, and in response to the endoscope being moved during image capture, the circuitry generates the image data so that a display range of a corresponding image displayed on a display device does not substantially change.

(2)

The image processing device according to (1), wherein the circuitry is configured to crop and enlarge captured images from the endoscope a predetermined distance from a center of the captured images obtained during the movement and after the movement of the endoscope, and generate the image data during the movement and after the movement.

(3)

The image processing device according to (1), wherein the image captured by the endoscope is a video image.

(4)

The image processing device according to (1), wherein the endoscope is moved in an optical axis direction of an objective lens of the endoscope.

(5)

An endoscopic surgery system including:
 an image processing device including circuitry configured to generate image data from an image captured by an endoscope of an inside of a body of a patient, and in response to the endoscope being moved during image capture, the circuitry generates the image data so that a display range of a corresponding image displayed on an external display device does not substantially change; and
 an arm control device that controls driving of a supporting device that supports the endoscope with an arm unit, and moves a lens barrel of the endoscope,
 in response to a predetermined retraction condition being satisfied, the circuitry is configured to issue an instruction to the arm control device to execute a retraction operation to move the lens barrel in a retraction direction, which is an optical axis direction of an objective lens and in which the lens barrel is moved away from an observation target site, and in response to a predetermined return condition being satisfied, the circuitry is configured to issue an instruction to the arm control device to execute a return operation to move the lens barrel in a return direction, which is the optical axis direction of the objective lens and in which the lens barrel comes near the observation target site, when a predetermined return condition is satisfied.

(6)

The endoscopic surgery system according to (5), wherein the retraction condition is detection from the captured image of mist generation, and the return condition is a detection of at least a partial disappearance of the mist from the captured image.

(7)

The endoscopic surgery system according to (6), wherein, when generation of the mist is detected, a leading end of an energy device is detected as being present in the captured image, and the generation of the mist is detected in a predetermined range about the detected leading end of the energy device.

(8)

The endoscopic surgery system according to (5), wherein the retraction condition is that mist presence areas occupy a first predetermined ratio or more of the captured image, and the return condition is that the mist presence areas occupy a second predetermined ratio or less of the captured image.

(9)

The endoscopic surgery system according to (5), wherein the retraction condition is that a distance between a treatment instrument and a treatment site is a first predetermined threshold value or shorter, and the return condition is that the distance between the treatment instrument and the treatment site is a second predetermined threshold value or longer.

(10)

The endoscopic surgery system according to (5), wherein the retraction condition is that an energy device is energized, and the return condition is that output of the energy device has stopped and at least partial disappearance of mist is detected based on the captured image.

(11)

The endoscopic surgery system according to (5), wherein the retraction condition is that manipulation in which an operator performs treatment with an energy device is made, and the return condition is that manipulation in which the operator ends the treatment with the energy device is made.

(12)

The endoscopic surgery system according to (5), wherein the retraction condition is that a grip mechanism at a leading end of a treatment instrument is detected to have gripped a part of a biological tissue based on the captured image, and the return condition is that the grip mechanism at the leading end of the treatment instrument is detected to have released the part of the biological tissue based on the captured image and disappearance of mist is detected based on the captured image.

(13)

The endoscopic surgery system according to (5), wherein the retraction condition and the return condition include detection of a user-initiated instruction.

(14)

The endoscopic surgery system according to (5), wherein the retraction condition is that a distance between a leading end of the endoscope and a treatment instrument is a first predetermined threshold value or shorter, and the return condition is that the distance between the leading end of the endoscope and the treatment instrument is a second predetermined threshold value or longer.

(15)

The endoscopic surgery system according to (5), wherein a movement amount of the lens barrel at the time of the return operation is a same value as a movement amount of the lens barrel at the time of the retraction operation.

(16)

The endoscopic surgery system according to (5), wherein a movement amount of the lens barrel at the time of the return operation is a value obtained by subtracting a distance between a leading end of the lens barrel and an observation target site immediately before generation of mist is detected, from a distance between the leading end of the lens barrel and the observation target site at which the mist does not obscure the captured image.

(17)

The endoscopic surgery system according to (5), wherein the retraction operation and the return operation are executed as the arm control device controls rotation of a plurality of joints constituting the arm unit in a coordinated manner.

(18)

The endoscopic surgery system according to (5), wherein the endoscope is supported in a manner that the lens barrel is inserted into a cylindrical holding unit provided at a leading end of the arm unit,
the holding unit includes a slider mechanism that holds the lens barrel movably in a stretching direction and an actuator that causes the slider mechanism to operate and urge the lens barrel in the stretching direction, and
the retraction operation and the return operation are executed when the actuator causes the slider mechanism to operate under control of the arm control device.

(19)

The endoscopic surgery system according to (5), wherein the arm control device performs power-assist control to drive the arm unit to assist an external force from an operator.

(20)

The endoscopic surgery system according to (19), wherein the arm control device drives the support arm device to generate assist force that encourages a movement manipulation of the lens barrel in the retraction direction at the time of the retraction operation, and drives the support arm device to generate assist force encouraging a movement manipulation of the lens barrel in the return direction at the time of the return operation.

(21)

The endoscopic surgery system according to (19), wherein the circuity processes the image data to cause a distance between a leading end of the lens barrel and an observation target site to be superimposed and displayed on the display image at the time of the retraction operation and the return operation.

(22)

An image processing method including:
generating with circuitry image data from an image captured by an endoscope of an inside of a body of a patient, and in response to the endoscope being moved during image capture, the circuitry generating the image data so that a display range of a corresponding image displayed on an external display device does not substantially change.

REFERENCE SIGNS LIST 1, 1a, 1b, 2 image processing system
111 image sensor
112 focus adjustment mechanism
113 distance detection unit
121, 121a, 121b, 121c movement control unit
122 image processing unit
123 focus control unit
131 actuator driving control unit
141 actuator
3000 endoscopic surgery system
3100 endoscope
3101 lens barrel
3200 surgical instrument
3203 energy device
3300 support arm device
3401 CCU
3403 display device
3407 arm control device
3409 input device

The invention claimed is:

1. An image processing device, comprising:
circuitry configured to:
generate first image data from a first image captured by an endoscope, wherein
the endoscope is at a first position, and
the first image is an image of an inside of a body of a patient;
control display of the generated first image data on a display device;
crop an area from a second image captured by the endoscope, wherein
the second image is captured after movement of the endoscope from the first position to a second position,
the cropped area corresponds to a display range of the displayed first image data,
the second image has a photographic range greater than the first image, and
a center of the cropped area is same as a center of the second image;
enlarge the cropped area;
generate second image data based on the enlarged cropped area; and
control display of the generated second image data on the display device, wherein the display range of the displayed first image data is substantially same as a display range of the displayed second image data.

2. The image processing device according to claim 1, wherein the first image is a video image.

3. The image processing device according to claim 1, wherein the circuitry is further configured to control movement of the endoscope in an optical axis direction of an objective lens of the endoscope.

4. An endoscopic surgery system, comprising:
an endoscope configured to:
capture a first image at a first position, wherein the first image is an image of an inside of a body of patient; and
capture a second image at a second position based on movement of the endoscope from the first position to the second position, wherein
the second image has a photographic range greater than the first image, and
the endoscope includes a lens barrel;
an image processing device including circuitry configured to:
generate first image data from the first image;
control display of the generated first image data on a display device;
crop an area from the second image, wherein
the cropped area corresponds to a display range of the displayed first image data, and
a center of the cropped area is same as a center of the second image;
enlarge the cropped area;
generate second image data based on the enlarged cropped area; and
control display of the generated second image data on the display device, wherein the display range of the displayed first image data is substantially same as a display range of the displayed second image data; and
an arm control device configured to control movement of an arm unit and the lens barrel, wherein
the circuitry is further configured to:
issue, based on a retraction condition, a first instruction to the arm control device to execute a retraction operation to move the lens barrel of the endoscope in a retraction direction from the first position to the second position, wherein
the retraction direction is an optical axis direction of an objective lens of the lens barrel, and
the second position is away from an observation target site than the first position; and
issue, based a return condition, a second instruction to the arm control device to execute a return operation to move the lens barrel in a return direction from the second position to the first position, wherein
the return direction is the optical axis direction of the objective lens, and
the lens barrel is movable from the second position to the first position near the observation target site.

5. The endoscopic surgery system according to claim 4, wherein
the retraction condition is detection of mist from the first image, and
the return condition is a detection of at least a partial disappearance of the mist from the second image.

6. The endoscopic surgery system according to claim 5, wherein, when generation of the mist is detected, a leading end of an energy device is detected as being present in the captured image, and the generation of the mist is detected in a predetermined range about the detected leading end of the energy device.

7. The endoscopic surgery system according to claim 4, wherein the retraction condition is that mist presence areas occupy a first predetermined ratio or more of the captured image, and the return condition is that the mist presence areas occupy a second predetermined ratio or less of the captured image.

8. The endoscopic surgery system according to claim 4, wherein the retraction condition is that a distance between a treatment instrument and a treatment site is a first predetermined threshold value or shorter, and the return condition is that the distance between the treatment instrument and the treatment site is a second predetermined threshold value or longer.

9. The endoscopic surgery system according to claim 4, wherein the retraction condition is that an energy device is energized, and the return condition is that output of the energy device has stopped and at least partial disappearance of mist is detected based on the captured image.

10. The endoscopic surgery system according to claim 4, wherein the retraction condition is that manipulation in which an operator performs treatment with an energy device is made, and the return condition is that manipulation in which the operator ends the treatment with the energy device is made.

11. The endoscopic surgery system according to claim 4, wherein the retraction condition is that a grip mechanism at a leading end of a treatment instrument is detected to have gripped a part of a biological tissue based on the captured image, and the return condition is that the grip mechanism at the leading end of the treatment instrument is detected to have released the part of the biological tissue based on the captured image and disappearance of mist is detected based on the captured image.

12. The endoscopic surgery system according to claim 4, wherein the retraction condition and the return condition include detection of a user-initiated instruction.

13. The endoscopic surgery system according to claim 4, wherein the retraction condition is that a distance between a leading end of the endoscope and a treatment instrument is a first predetermined threshold value or shorter, and the return condition is that the distance between the leading end of the endoscope and the treatment instrument is a second predetermined threshold value or longer.

14. The endoscopic surgery system according to claim 4, wherein a movement amount of the lens barrel at a time of the return operation is a same value as a movement amount of the lens barrel at a time of the retraction operation.

15. The endoscopic surgery system according to claim 4, wherein a movement amount of the lens barrel at a time of the return operation is a value obtained by subtracting a distance between a leading end of the lens barrel and an observation target site immediately before generation of mist is detected, from a distance between the leading end of the lens barrel and the observation target site at which the mist does not obscure the captured image.

16. The endoscopic surgery system according to claim 4, wherein the arm control device is further configured to:
control rotation of a plurality of joints of the arm unit in a coordinated manner; and
execute, based on the rotation of the plurality of joints, the retraction operation and the return operation.

17. The endoscopic surgery system according to claim 4, further comprising:
a cylindrical holding unit, wherein
the lens barrel is inserted into the cylindrical holding unit,
the cylindrical holding unit is at a leading end of the arm unit, and
the cylindrical holding unit is configured to:
hold the lens barrel movably in a stretching direction; and
operate and urge the lens barrel in the stretching direction.

18. The endoscopic surgery system according to claim 4, wherein the arm control device is further configured to drive the arm unit to assist an external force from an operator.

19. The endoscopic surgery system according to claim 18, wherein the arm control device is further configured to:
control generation of assist force that encourages a movement manipulation of the lens barrel in the retraction direction at a time of the retraction operation, and
control generation of assist force that encourages a movement manipulation of the lens barrel in the return direction at a time of the return operation.

20. The endoscopic surgery system according to claim 18, wherein
the circuitry is further configured to process specific image data to superimpose, at a time of the retraction operation and the return operation, cause a distance between a leading end of the lens barrel and the observation target site on a specific image displayed on the display device.

21. An image processing method, comprising:
generating, by circuitry, image data from a first image captured by an endoscope, wherein
the endoscope is at a first position, and
the first image is an image of an inside of a body of a patient;
controlling, by the circuitry, display of the generated first image data on a display device;
cropping, by the circuitry, an area from a second image captured by the endoscope, wherein
the second image is captured after movement of the endoscope from the first position to a second position,
the cropped area corresponds to a display range of the displayed first image data,
the second image has a photographic range greater than the first image, and
a center of the cropped area is same as a center of the second image;
enlarging, by the circuitry, the cropped area;
generating, by the circuitry, second image data based on the enlarged cropped area; and
controlling, by the circuitry, display of the generated second image data on the display device, wherein the display range of the displayed first image data is substantially same as a display range of the second image data.

* * * * *